(12) United States Patent
Hasegawa et al.

(10) Patent No.: US 10,215,700 B2
(45) Date of Patent: Feb. 26, 2019

(54) PLASMONIC CHIP FOR OBSERVING CANCER RELATED SUBSTANCES BY LOCALIZED SURFACE PLASMON RESONACE

(71) Applicant: MYTECH CO., LTD., Hyogo (JP)

(72) Inventors: Yuki Hasegawa, Hyogo (JP); Katsuyuki Hasegawa, Hyogo (JP)

(73) Assignee: MYTECH CO., LTD., Hyogo (JP)

(*) Notice: Subject to any disclaimer, the term of this patent is extended or adjusted under 35 U.S.C. 154(b) by 0 days.

(21) Appl. No.: 15/346,078

(22) Filed: Nov. 8, 2016

(65) Prior Publication Data

US 2017/0115216 A1    Apr. 27, 2017

Related U.S. Application Data

(63) Continuation of application No. PCT/JP2015/063219, filed on May 17, 2015.

(30) Foreign Application Priority Data

Feb. 26, 2015  (JP) .................................. 2015-036645

(51) Int. Cl.
G01N 21/47       (2006.01)
G01N 21/552      (2014.01)
(Continued)

(52) U.S. Cl.
CPC ......... *G01N 21/554* (2013.01); *G01N 21/648* (2013.01); *G01N 21/6458* (2013.01);
(Continued)

(58) Field of Classification Search
CPC .... G01N 21/554; G01N 21/65; G01N 33/574; G01J 3/44; G02B 5/008
See application file for complete search history.

(56) References Cited

U.S. PATENT DOCUMENTS 8,810,789 B2 *  8/2014  Zhao ..................... G01J 3/4412
                                                356/301
2011/0275061 A1  11/2011  Weidemaier et al.
(Continued)

FOREIGN PATENT DOCUMENTS

JP    2010-517582 A    5/2010
JP    2010-537155 A    12/2010
(Continued)

OTHER PUBLICATIONS

Internatinal Saearch Report dated Aug. 4, 2015 issued in corresponding PCT/JP2015/0633219 application.

*Primary Examiner* — Maurice Smith
(74) *Attorney, Agent, or Firm* — IP Business Solutions, LLC

(57) ABSTRACT

A cancer-related substance in blood or a biological sample can be detected in a selective manner, so it becomes possible to determine the occurrence of cancer by observation of fluorescent image of a crystal of the censor related substance or a coagulated state of the crystal on a plasmonic chip. In addition, the state of chemical modification of a histone tail can be determined by a Raman spectrum analysis. Furthermore, the location of the cancer-related substance aggregated on a substrate cannot be determined with naked eyes. Then, as a second aspect of the present invention, a method for diagnosing a cancer disease is provided, said method being characterized by firstly identifying the location of the region of a crystal by observing fluorescent image on a microscope, and then irradiating the crystal, with laser beam to analyze with respect to the chemical modification of a histone tail and a remodeling factor.

5 Claims, 24 Drawing Sheets

(51) Int. Cl.
  *G01N 33/49*    (2006.01)
  *G01N 21/64*    (2006.01)
  *G01N 21/65*    (2006.01)

(52) U.S. Cl.
  CPC ....... *G01N 21/6486* (2013.01); *G01N 21/658* (2013.01); *G01N 33/49* (2013.01)

(56) References Cited

U.S. PATENT DOCUMENTS

| | | |
|---|---|---|
| 2012/0115245 A1 | 5/2012 | Hasegawa et al. |
| 2013/0230660 A1 | 9/2013 | Hase et al. |
| 2013/0244337 A1* | 9/2013 | Meinhart .......... G01N 33/0011 436/164 |
| 2014/0333723 A1 | 11/2014 | Dowaki et al. |

FOREIGN PATENT DOCUMENTS

| | | | | |
|---|---|---|---|---|
| JP | 2011-158369 A | | 8/2011 | |
| JP | WO2014181816 | * | 5/2013 | ............... C01G 5/00 |
| JP | 2013-133475 A | | 7/2013 | |
| JP | 2013-178224 A | | 9/2013 | |
| JP | 2014-219623 A | | 11/2014 | |
| JP | WO2014181814 | * | 11/2014 | ........... G01N 21/658 |
| JP | 2014-238382 A | | 12/2014 | |
| WO | 2010/101209 A1 | | 9/2010 | |
| WO | 2011/11472 A1 | | 1/2011 | |
| WO | 2012/033097 A1 | | 3/2012 | |
| WO | 2013/039180 A1 | | 3/2013 | |
| WO | 2013/065747 A1 | | 5/2013 | |
| WO | 2014/181814 A1 | | 11/2014 | |
| WO | 2014/181816 A1 | | 11/2014 | |

\* cited by examiner (a)      (b)

PLASMONIC CHIP FOR OBSERVING CANCER RELATED SUBSTANCES BY LOCALIZED SURFACE PLASMON RESONACE

CROSS-REFERENCE TO RELATED APPLICATIONS

This application is a continuation application of International Patent Application No. PCT/JP2015/063219 filed on May 7, 2015 which claims priority to International Patent Application No. PCT/JP2014/062318 filed on May 8, 2014. The International Patent Application No. PCT/JP2014/062318 claims priority to Japanese Patent Application No. 2015-036645 filed on Feb. 26, 2015. The entire content of International Patent Application No. PCT/JP2014/062318 and Japanese Patent Application No. 2015-036645 is incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

Field of the Invention (Technical Field)

The present invention relates to a method of measuring cancer-related substances which increase in blood with the progress of cancer, including mainly a free DNA (DNA wrapped around the histones) as a target to be measured by Raman spectroscopy.

Description of Related Art

A method of measuring a cancer-related substance which increases in the blood with the progress of the disease has hitherto been used as a diagnostic method for cancer. The cancer-related substances referred to proteins and the like, which are cancer-specific substances extracted from a body fluid of cancer patients and are generally released into the blood when the cancer cells are destroyed. According to the prior diagnostic methods of the cancer, it is determined that there is a possibility that the test subject or patient is suffering from cancer when more than a determined value of the cancer-related substance is found existing in the blood.

Thus, as the cancer-related substance released into the blood by destruction of the cancer cells, it is known that not only proteins but also DNA may be released into the blood. And, when compared with the healthy subjects and cancer patients, it has been reported that the amount of the free DNA (ctDNA) derived from cancer cells in blood, is significantly more in those cancer patients than healthy individuals. Thus, by quantifying the free DNA of cancer cells from the body fluid such as blood, it is considered to be able to diagnose the presence of cancer. As such a method of cancer diagnosis, for example, there are proposed 1) a method of diagnosing a possibility of cancer in case of detecting 200 bp or more of DNA to be amplified by the polymerase chain reaction (PCR) method and the like, in the body fluid or feces discharged from the body, and further analyzing a mutation in its DNA if necessary (Patent Document 1 and 2), and 2) a method of quantifying genomic DNA contained in a body fluid, and further performing DNA testing in the case of more than a predetermined value of the genomic DNA (Patent Document 3).

Furthermore, even if the patient is diagnosed suffering from cancer, mere quantitative analysis of the DNA in body fluids is unable to identify a cancer suffering organ. When the cancer is arising and progressing, it is known that a specific mutation of DNA occurs depending on the original cancer site. Therefore, by clarifying the type of mutation in the DNA, it may be possible to identify an organ or a cancer site where the cancer is developing. Here, as Mutations of DNA, there are listed point mutations of DNA and also structural abnormalities such as chromosome gain or loss. For example, in about 70% of pancreatic cancer, it is known that the point mutation occurs in the K-ras gene. Also, in the analysis of loss of heterozygous, (hereinafter referred to as LOH) there have been reported the loss of specific chromosomal arms depending on each cancer type, for example, it is known that LOH is concentrated on the short arm of chromosome 3 in case of the lung cancer. Also, the amplification of long arm No. 8 of chromosome and the amplification of RB2 are known in the breast cancer. Therefore, in order to provide an improved method for diagnosing cancer with high accuracy by quantifying the free DNA from cancer cells with a biochip as described herein, there has been provided a method of diagnosing cancer, which comprises a step of extracting a free DNA from plasma collected from a subject, a step of calculating the free DNA per unit volume of the extracted plasma by quantifying the free DNA, a step of comparing the calculated value of the free DNA with a second threshold value more than the first threshold value, a step of making a diagnose as follows; the subject has a high possibility of affection with cancer when the calculated value is less than the first threshold value, while some DNA from normal cells are mixed in the plasma when the above threshold is more than the second threshold value (patent document 4).

(Patent Document 1) Japanese Patent Application Publication No. 2010-517582
(Patent Document 2) International Patent Application Publication No. WO2011-11472
(Patent Document 3) Japanese Patent Application Publication No. 2011-158369
(Patent Document 4) International Patent Application Publication No. WO2013-039180
(Non-Patent Document 1) J G Herman, Seminars in Cancer Biology, 9: 359-67, 1999

THE SUMMARY OF THE INVENTION

Problem to be Solved by the Invention

However, mass production of a plasmonic chips is not easy and also adsorption of cancer-related substance or fluorescence-labeled markers onto the mass-produced plasmonic chip is not easy, so that it is difficult to exert the fluorescence enhancement effect on the present plasmonic chips. Accordingly, the present invention is to provide a plasmonic chips which is easy to be mass produced, whereby cancer-related substances or fluorescent labeling marker of adsorbent material such as antibody and so on, can be absorbed onto the plasmonic chips, so that plasmons on plasmonic chips can enhance the emission of fluorescence intensity from several times to several tens of times so as to realize a diagnostic method for cancer diseases by using a diagnosed fluorescence image on the plasmonic chip.

According to the present invention, there can be provided firstly substrates of 1) silver complex quantum crystals and 2) silver peroxide meso crystals prepared by alkali treatment of the silver complex quantum crystals, which realize not only a physical property of localized surface plasmon resonance (LSPR) by light irradiation including UV, and infrared light, but also a chemical property which enables to absorb an antibody, fluorescent label markers and ligands with fluorescent label markers as a kind of ligands when silver complex quantum crystals are prepared. On the other hand, silver peroxide meso crystal has an another chemical property to absorb the cancer-related substances, such as nucleosome or chromatin including the DNA in the serum, particularly a histone wrapped around with DNA. Therefore, the present invention can be made on the findings that a plasmonic chip can be used for observing a fluorescence image under a fluorescence microscope, to judge or detect the presence or absence of cancer by selective absorption of cancer makers or nucleosome and clomatine as cancer-related substance. According to the present invention, there can be provided a plasmonic chip where a region of quantum crystal of plasmon metal complexes is formed on the substrate to selectively absorb or capture tumor makers with cancer related substance and to be enhanced by the localized surface plasmon resonance function. Further, according to the present invention, there can be provided a plasmonic chip where a region of meso-crystal of nanocrystal of silver oxide or oxides containing silver peroxides made from quantum crystal of silver complex, is formed on a metal substrate by alkali treatment wherein the meso-crystal is able to absorb or capture the cancer-related substance and to be enhanced by localized surface plasmon resonance function by light irradiation in the crystal area so as to observe the auto fluorescence image.

According to the present invention, there can be secondly provided a method of performing imaging of cancer diseases using the plasmonic chips, which comprises a step of providing a plasmonic chip which has a meso-crystal region is prepared by alkali treatment from the silver complex quantum crystals and contains silver oxide nanocrystals containing silver peroxides; a step of adding dropwise a serum or biological liquid sample on the crystalline regions of the plasmonic chips, to selectively absorb capture cancer-related substances having a positively charged protein molecules in the sample; a step of irradiating the agglomerated crystals on the plasmonic chip with light to observe the auto fluorescence image for diagnosis of the presence or absence of cancer. On the other hand, according to the present invention, there can be provided another method, which comprises a step of providing a silver complex quantum crystal on the metal substrate having an electrode potential less noble than that of a reduction potential of silver complex, where the tumor marker having a fluorescent function with ligand of the metal complex quantum crystal or as one of the ligand was added to place the tumor markers in the crystalline region in the silver complex quantum crystals, and a step of light irradiating the silver complex quantum crystal region to enhance the fluorescence emission intensity of the tumor markers by localized surface plasmon resonance and a step of observing the fluorescence image of a cancer disease.

In addition, the position of the cancer-related substances aggregated on the substrate cannot be determined visually. According to the present invention, there can be provided a cancer diagnostic method which is characterized in that determination of the location of its crystalline region is made by distinct vision image with a microscope under a laser irradiation and then analyzation of chemical modification of histone tails, and remodeling factors can be made (FIG. 19). Thirdly, according to present invention, there can be provided a cancer diagnostic method of Raman spectroscopy, which comprises a step of observing a fluorescence image of the cancer-related substances captured on the plasmonic chip as a mark for a laser irradiation, and a step of irradiating the fluorescence image with various laser lights of 514 nm, 532 nm, 633 nm, and 785 nm for the precise analysis. Accordingly, the present invention relates to a method of diagnosing a body fluid, in particular selectively captured cancer-related substances in the blood, as well as a method of analyzing the structure of a histone or chromatin, by analyzing the factors that chemical modification of histones tails, existence of cancers. The method is intended to enable early stage diagnosis of cancer as well as the presence or absence of the cancer.

According to the present invention, the plasmonic chips, make it possible to selectively adsorb the cancer-related substances or tumor markers, so that localized surface plasmon resonance makes fluorescence intensity of the fluorescence image enhanced, whereby it is possible to facilitate the determination of the cancer diagnosis from the fluorescence images. By the way, less noble electrode potential (larger ionization tendency) of the metal substrate than the metal complex causes a potential difference to make aggregation of quantum crystals (nano-sized metal complex crystals) from the metal complex solution by means of chemical reduction. In case of silver complex, quantum crystals of silver complex can be formed by the chemical reduction where aggregation of quantum crystals of silver complex on the metal substrate from silver thiosulfate aqueous solution is caused by noble electrode potential (higher ionization tendency) of silver than that of copper or copper alloy. In detail, the concentration of the metal complex in the aqueous solution should be mainly determined in the light of the size of the quantum crystals to be formed, so the concentration of a dispersing agent, if used, has to be considered. Although 100 to 5000 ppm can be used, 500 to 2000 ppm is preferred for preparation of nano-sized crystals to say the nanocluster depending on the functionality of the ligand.

Metal complex to be formed as a quantum crystal is selected in the light of a complex stability constant (log ß) according to the following formula (I) to correlate the electrode potential E of the supported metal.

$$E°=(RT/|Z|F)\ln(ßi) \qquad \text{Formula (I)}$$

(Where E° is the standard electrode potential, R is the gas constant, T is absolute temperature, Z is ion valence, F represents the Faraday constant.).

In case of complexes of a plasmon metal selected from the group consisting of Au, Ag, Pt and Pd, an enhancement effect caused by localized surface plasmon resonance can be obtained by irradiation of the Raman light. In particular, in case of silver complexes the silver complexes may be formed by a reaction which may be preferably carried out between a silver complexing agent having a stability constant (formation constant) (log ßi) of 8 or more and silver halide, preferably silver chloride. The complexing agent can be selected from the group consisting of thiosulfate, thiocyanate, sulfite, thiourea, potassium iodide, and thiosalicylic acid salt. The silver complexes become quantum crystals of 100~200 nm provided with quantum dots made of nanoclusters having average diameter of 5~20 nm.

It is believed that alkaline treatment (with an aqueous solution of sodium hypochlorite) makes silver complex quantum crystals to be changed into needle-like or acicular nanocrystals of silver oxide composite, containing a silver peroxide as a core of silver halide by the following reaction (FIG. 5). The silver oxide composite shows a minus (−) charge in water while a histone wound around with DNA shows a plus (+) charge (FIG. 7 (a)), whereby it is found that the positively charged cancer related substances including free nucleosomes are selectively adsorbed. Moreover, it is found that the acicular nanocrystals of silver oxides containing silver peroxides can be reduced by means of irradiation with a laser beam and further changed into the metallic silver, so as to show the surface plasmon enhancement effect by means of laser beam irradiation, which makes it possible to detect histones by the auto fluorescence of cancer-related substances.

$$Na_2S_2O_3 + 4NaClO + H_2O \rightarrow Na_2SO_4 + H_2SO_4$$
$$(2NaHSO_4) + 4NaCl$$

$$Ag^+ + NaCl \rightarrow AgCl + Na^+$$

$$Ag^+ + 3NaOCl \rightarrow 2AgCl + NaClO_3 + 2Na^+$$

$$Ag^+ + OH^- \rightarrow AgOH$$

$$2Ag^+ + 2OH^- \rightarrow Ag_2O + H_2O$$

According to the present invention, the needle-like nanocrystals of the silver oxide composite containing silver peroxides, can be formed by a self-organizing action or phenomenon as a neuron-like three-dimensional super-structure (so called meso crystals, referring to FIGS. 8 and 9). The silver oxide composite may be prepared by means of potentiostatic deposition using an Ag/AgCl electrode in silver ions aqueous solution and can be also prepared by oxidation of silver quantum crystals with an alkali treatment. For example, in case of silver thiosulfate, the silver complex quantum crystals can be easily prepared by the alkali treatment (with an aqueous solution of sodium hypochlorite).

Moreover, according to the present invention, use of the plasmonic chip, makes it possible to detect the presence of cancer-related substances in a biological sample including a blood and also to determine the chemical modification state where chromatin remodeling is controlled, through the fluorescence imaging diagnosis. That is, according to the present invention, the method comprises a step of providing a plasmonic chip with a needle-like nanocrystal composites of the silver oxides containing silver halides or halogens, that is, a step of providing a plasmonic chip having a meso crystal region of the silver oxides containing silver peroxides (FIGS. 8 and 9), a step of dropping a plasma serum or biological sample solution onto the needle-like nano-crystal area on the plasmonic chip, so as to selectively absorb or capture the cancer-related material having a positive charge in the sample.

(Diagnostic Imaging of Plasmonic Chips On Crystal)

The absorbed cancer-related substances can be observed by irradiation of a laser of UV, red or green on with a fluorescence microscope (magnification 50 times). The fluorescence images of the cancer-related substances are shown in FIGS. 1 (a), (b) and (c) in case of gastric cancer and in FIGS. 2 (a), (b) and (c) in case of colorectal cancer while no fluorescence images of the samples can be shown in case of benign disease. The geometry, brightness and dimension of the fluorescence images can be quantified and the resulting numerical values are subjected to histogram processing. When observed with a fluorescence microscope, the crystal shapes between the benign disease and the gastric cancer or the colon cancer can show some differences. Therefore, it is understood that use of plasmonic chips provided with meso crystals containing silver peroxide or peroxides, makes it possible to selectively absorb or capture the cancer-related substances in blood and to determine the presence or absence of cancer by fluorescence image observation.

(Diagnostic Imaging of Tumor Marker on the Plasmonic Chip)

Although crystal of adsorbed tumor marker on the plasmonic chips cannot be visually observed, irradiation of ultraviolet, red, or green laser makes it possible to observe the crystals with a fluorescence microscope (50 times), where point-like dispersed crystalline masses can be observed. Detection of the Raman spectra therefrom by irradiating of various laser beams makes it possible to determine the cancer disease with the intensity of surface-enhanced Raman scattering (SERS).

(Selective Capture of Cancer-Related Substances)

It is understood in the present invention that the cancer-related substances in serum may include, a histone wound around with DNA (so called nucleosomes), and also a chromatin (fiber) where histones gather and form a string-like structure. It is indicated that the substances to be detected in the present invention are deemed to be the cancer-related substances in the light of their increasing volumes because although globulin is positively charged, the globlin increases up to 2 times at most, while the cancer-related substance increases up to 100 times in association with progression of the cancer. Moreover, DNA left from the normal cells, DNA dissociated from histones by acetylation and albumin account for approximately 60% of serum, but owing to their negative charge, they will not be absorbed in the present invention. Therefore, it is advantageous for fluorescence imaging of cancer-related substances. In order to confirm this phenomenon, the following tests were carried out.

FIG. 15 shows photographs of 100-fold image, 3000-fold image, and 3D image in case of 10-fold and 100-fold dilution samples of benign disease, Gastric cancer, and Colon cancer. FIG. 16 show photographs of 100-fold image, 3000-fold image with undulation, and 3D image in case of Kato-III (gastric signet ring cell carcinoma). Then, Kato-III was cultured and from the cancer cell a double-stranded DNA, RNA and Protein were extracted. The (a, b, c) are photographs of 100-fold surface image, 3000-fold surface image, and 3D surface image of the Kato-III (gastric signet ring cell carcinoma), while the (d, e, f) are photographs of 100-fold image, 3000-fold image, and 3D image of the DNA extracted therefrom. The (g, h, I) are also photographs of 100-fold image, 3000-fold image, and 3D image of the RNA. The (j, k, l) show photographs of 100-fold image, 3000-fold (images and undulations) and the 3D image of the Protein, while the (m, n, o) are photographs of 100-fold image, 3000-fold image, and 3D image showing a surface structure of physically grounded cancer cells. FIG. 17 shows Raman scattering spectra on the meso-crystal plasmonic chips where they are chemical cultured cancer cells (a), DNA extracted therefrom (b), RNA (c), Protein (d), physically crushed cancer cells (e), serum (f) from gastric cancer patients, serum (g) from colorectal cancer patients and serum (h) from benign disease patients. Kato-III is gastric signet ring cell carcinoma, MKN-45 (poorly differentiated gastric cancer line), CW-2 (Japanese derived colon cancer cell line), PK45-P (human pancreatic cancer cell line), and NHDF-Neo (skin fibroblasts). Accordingly, it is understood from these results that the cancer-related substances are deemed to be selectively absorbed or captured and detected by the plasmonic chips of the present invention.

Moreover, according to the present invention, it is believed that needle-like nanocrystals (so called meso crystals of the silver oxide or oxides containing silver peroxide or peroxides) is provided with silver oxides containing silver peroxides which are easily negatively charged in an aqueous solution so as to form a charge transfer complex in contact with the sample (target molecules). Furthermore, the silver oxide can be reduced by a light energy to become metallic silver, which will have an enhancing effect by localized surface plasmon resonance with the metallic nanoparticles arranged regularly. Therefore, the needle-like nano-crystals (meso crystal) of the present invention, although it is a non-metal, are provided with an ionization property together with a metal property, which becomes a plasmonic chip suitable for measurement of surface-enhanced Raman scattering (SERS), as a cancer diagnostic chip.

It is believed that quantum crystals formed on a metal substrate or metal particles tend to have a positive polarity in an aqueous solution as a metal complex crystal, so their subjection to alkali treatment in the presence of halide ions is preferable to adjust the polarity of the chips by sodium hypochlorite solution having more than pH11 in order to fixedly adsorb the protein in a biological sample. According to the present invention, recrystallization of the quantum crystals makes it to have not only a negative polarity in an aqueous solution, but also makes it changed to needle-like composite of nanocrystal of silver oxides containing silver peroxides, so as to promote the histones having a positive charge in cancer-related substances absorbed on the chips.

BRIEF DESCRIPTION OF DRAWINGS

FIG. 15 shows RGB color histograms of 3000-fold image obtained by 3D laser scanning microscope in case of 10-fold dilution samples of Benign disease (s, t), Gastric cancer (u, v), and Colon cancer (w, x).

DESCRIPTION OF EMBODIMENTS

Hereinafter, embodiments of the present invention will be explained, referring to the attached drawings.

Example 1

Figure 4:
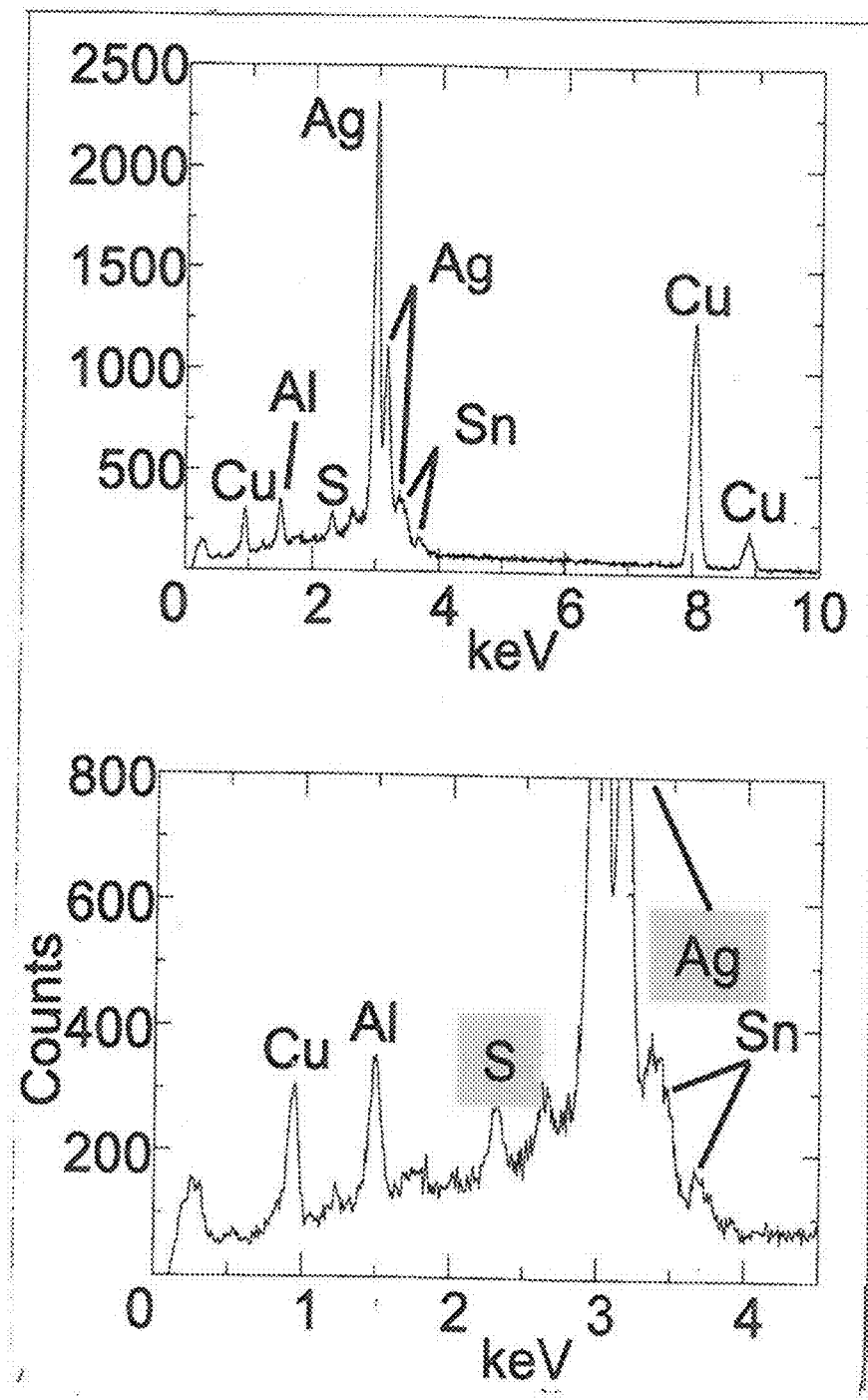
FIG. 4 is a graph showing a result of EDS spectra analysis of quantum crystals (elemental analysis).

As shown in FIG. 4, an aqueous solution containing 1000 ppm of silver thiosulfate was prepared and the 1 drop was added dropwise on a phosphor bronze plate. After standing for about 3 minutes, the solution on the plate was blown off. On the plate, quantum crystals were obtained as shown in the SEM image at the right side of FIG. 4.

Figure 5:
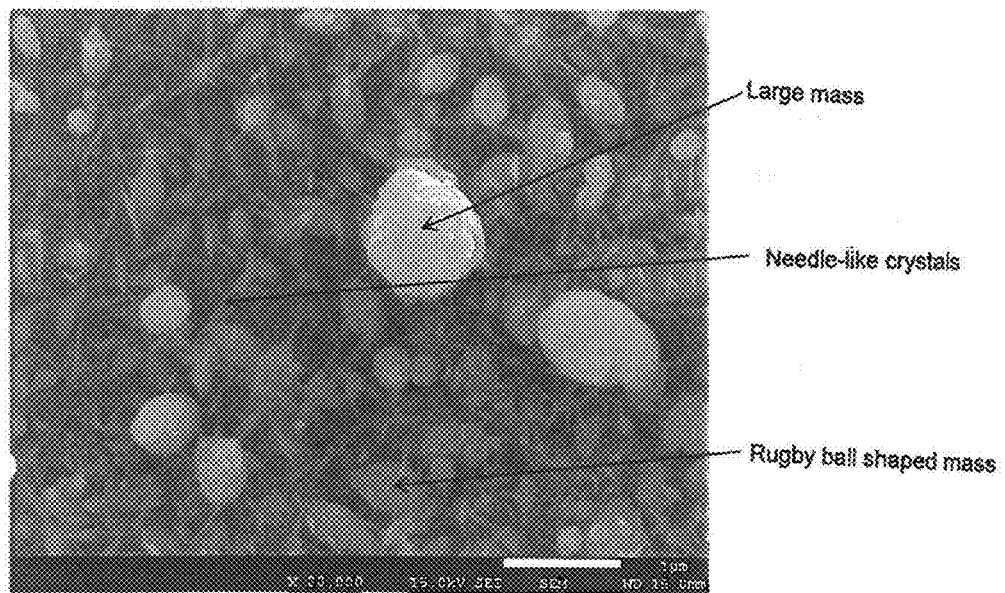
FIG. 5 is a photograph showing SEM image of quantum crystals alkali-treated in the presence of a halogen ion (Sodium hypochlorite treatment).
Figure 6A:
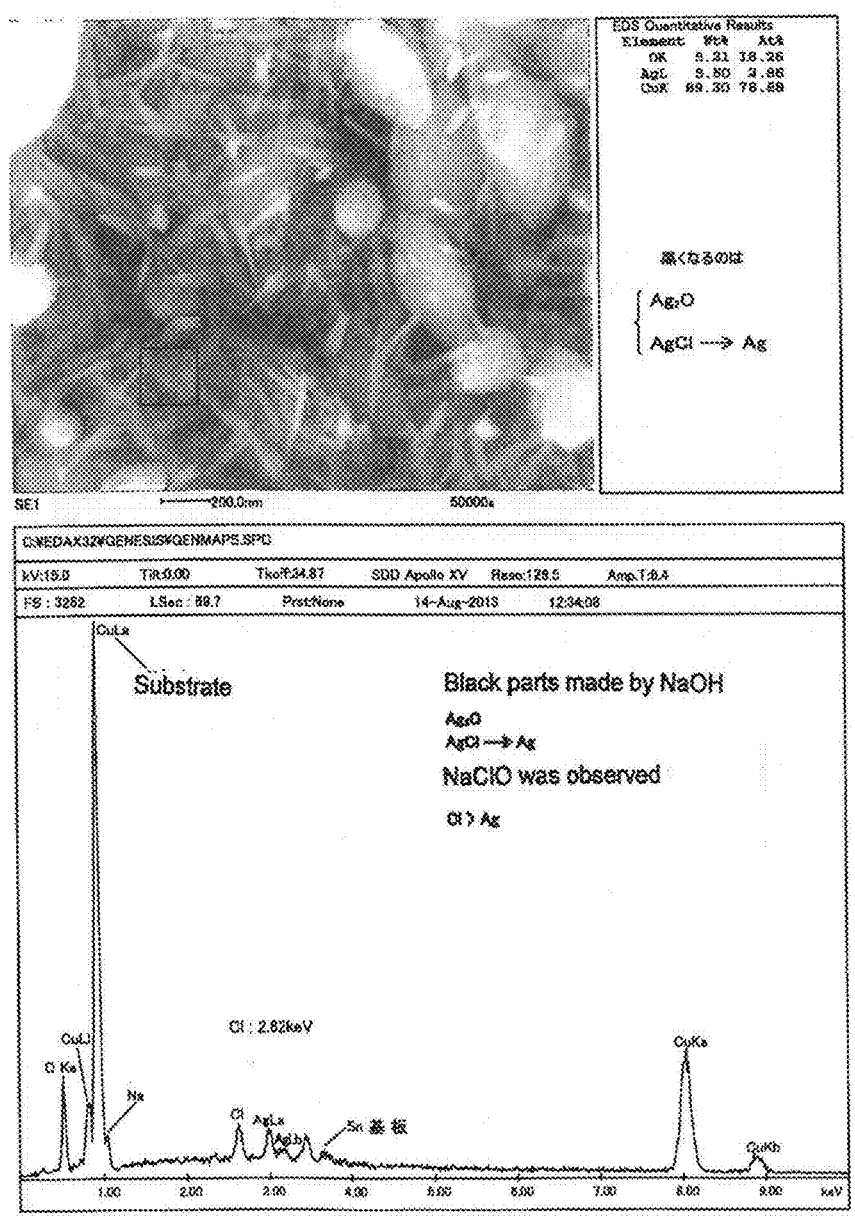
FIG. 6A is a photograph showing needle-like crystals of the alkali-treated quantum crystals.
Figure 6B:
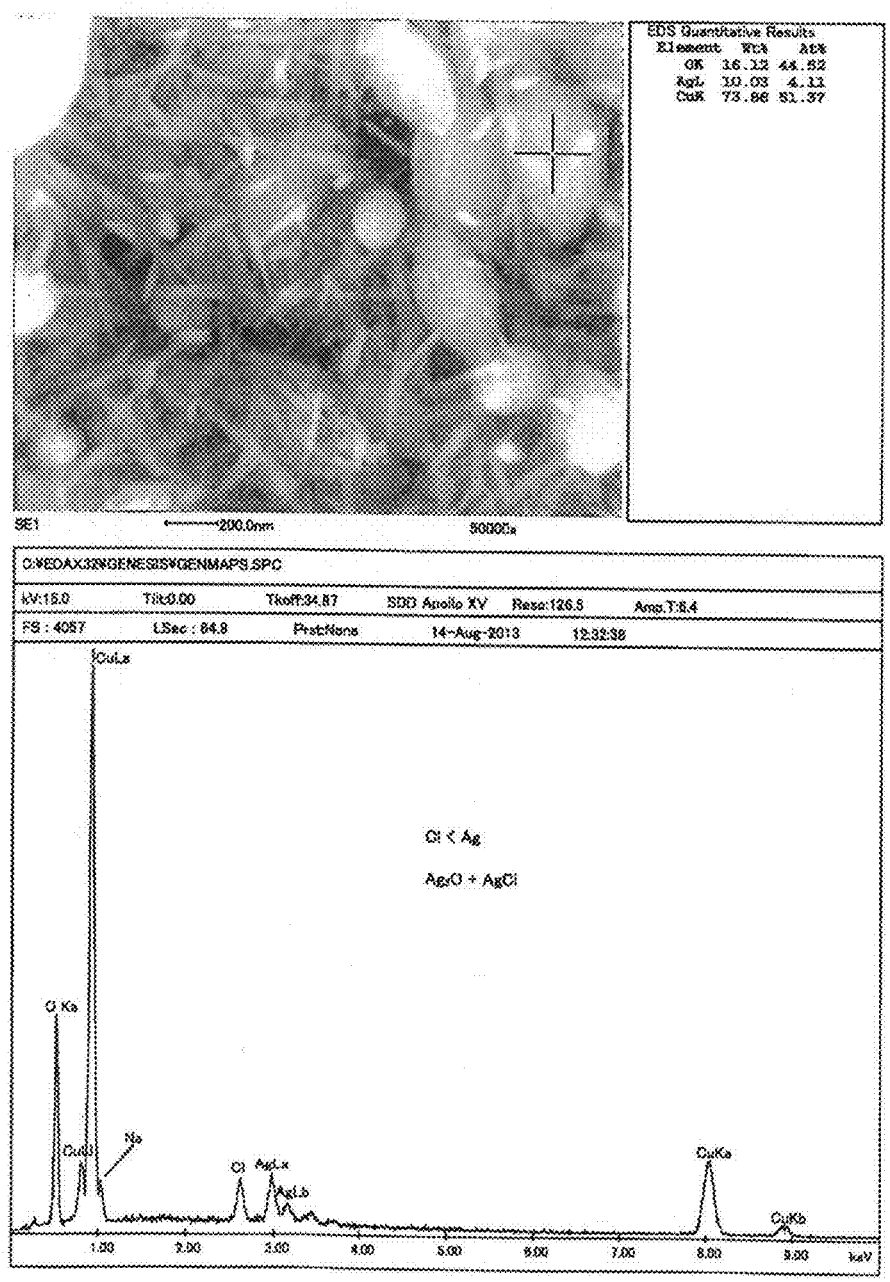
FIG. 6B is a photograph showing a rugby ball-shaped mass in the needle-like crystals.
Figure 6C:
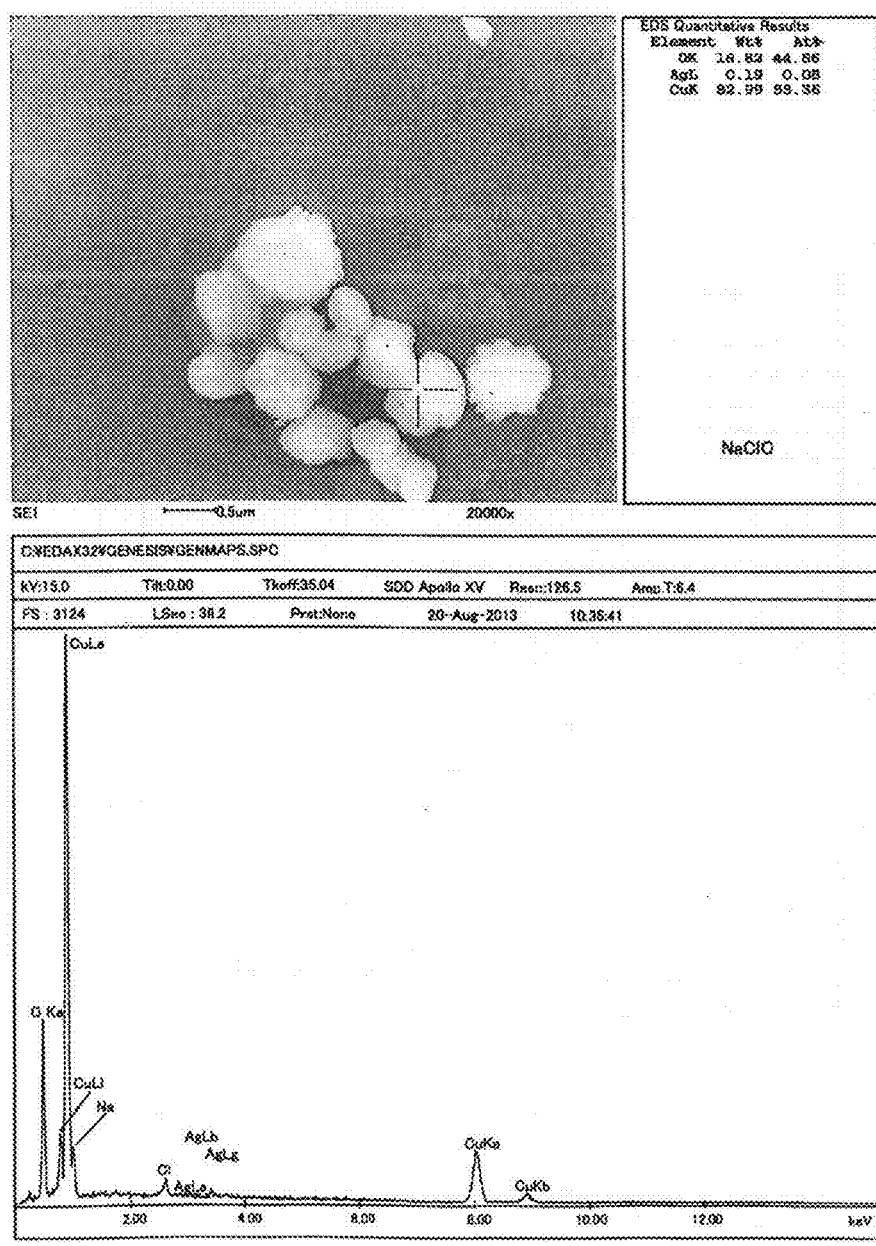
FIG. 6C is a graph showing a result of EDS spectra of large mass (elemental analysis).
Figure 7:
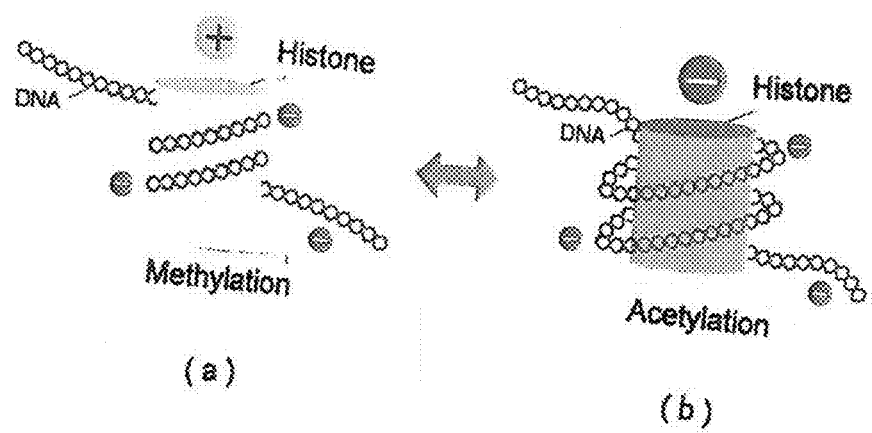
FIG. 7 is functional illustration views showing a state of the methylated free DNA (a) and a state of acetylated DNA (b).

FIG. 5 is a photograph showing various SEM images of the nano-particle aggregate prepared in Example 1 (quantum crystal), and FIG. 6 shows an enlarged SEM image of nano-particles where there were thin hexagonal columnar crystals of 100 nm more or less and having an unevenness surface of several nm order. We could not find out any specific facets of metal nano-crystals in the quantum crystals. FIG. 7 is a photograph showing the relationship between quantum crystal shapes and the standing time after dropping onto the phosphor bronze substrate, where it is recognized that firstly, a hexagonal quantum crystal is produced and then growing while maintaining the crystal shape.

Figure 8:
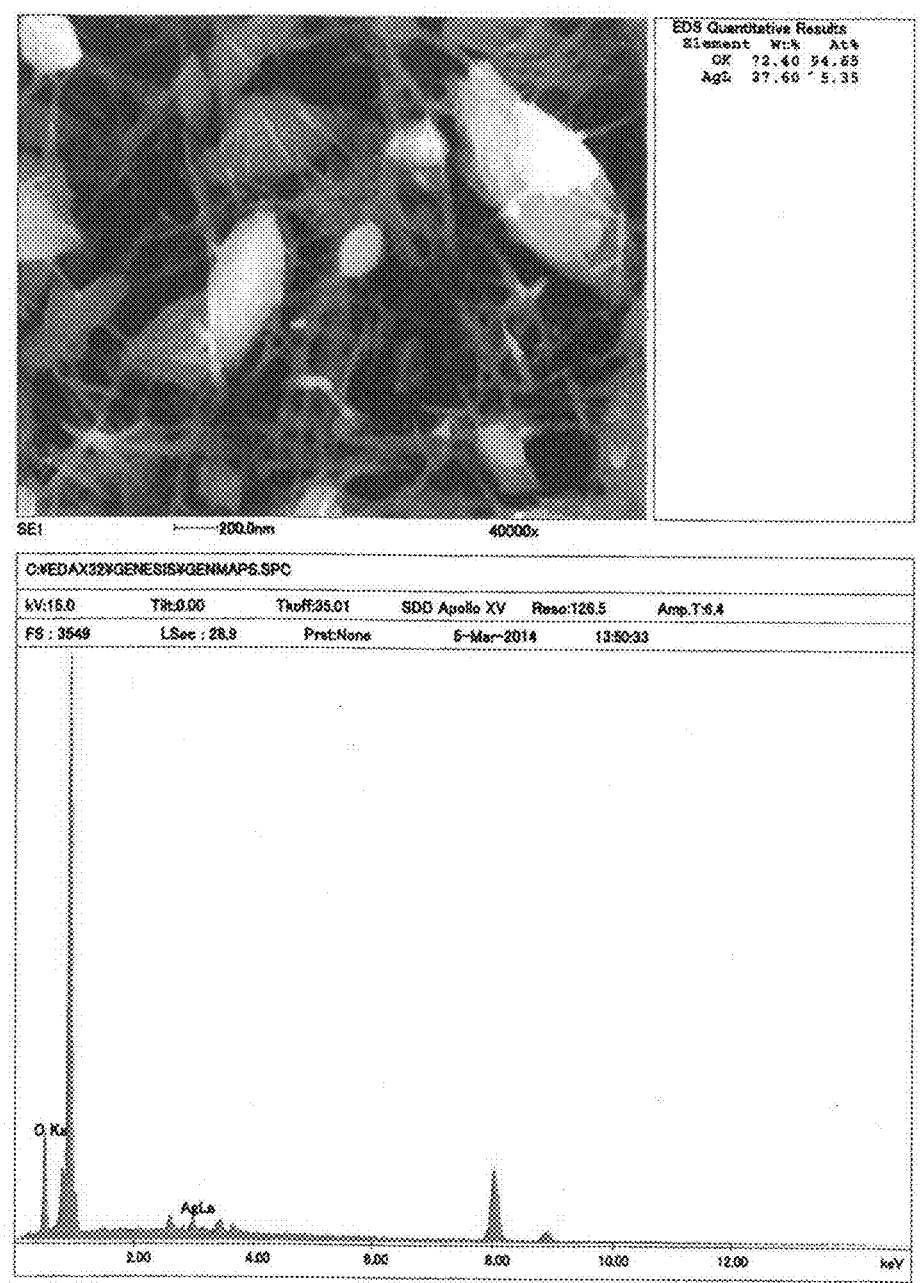
FIG. 8 is a view (top) of SEM image showing a re-crystallized substrate which is the quantum crystal substrate alkali treated in the presence of a halogen ion (Sodium hypochlorite treatment) (top view) and a graph (down view) showing a result (elemental analysis) of the EDS spectra of the re-crystallized substrate.

FIG. 8 is a graph showing a result of EDS spectra (elemental analysis) of the quantum crystals where not only silver but also elements derived from complex ligands can be detected in case of the quantum crystal on the phosphor bronze substrate, while only silver can be detected in the case of the quantum crystals formed on a copper plate by using 1000 ppm of silver thiosulfate in aqueous solution and keeping it for the standing time of 3 minutes after dropping onto the copper substrates.

(Discussion on Formation of the Quantum Crystal)

In case of 1000 ppm of silver thiosulfate complex in an aqueous solution, hexagonal column crystals of 100 nm more or less, are formed for the standing time of 3 minutes after dropping it onto a phosphor bronze plate, where it is confirmed that irregularities of several nm order are found on the hexagonal column quantum crystals from the SEM images (FIGS. 4, 5 and 6) and any specific facets derived from a metal nano-crystals are not found, while the EDS elemental analysis shows silver and elements derived from the complexing ligand. Accordingly, it can be estimated from the above analysis that the whole particles show nano-crystals of silver complex and also the unevenness appearance on the surface may be caused by the formation of spread quantum dots made of silver clusters in the complexes. From the aspect of phenomenon that the silver complex quantum crystals of the present invention can be formed on a phosphor bronze plate, while silver nano-particles alone can be deposited on the copper substrate, it is estimated that, as the equilibrium potential of the silver thiosulfate complexes is 0.33 which is equivalent to the copper electrode potential with 0.34, there is deposited only silvers with 0.80 on the copper substrate. On the other hand, in case of a phosphor bronze plate with the electrode potential of 0.22, which is slightly less noble than that of the copper so that silver complex crystals seem able to be precipitated. The concentration of the silver complex in the aqueous solution should be in a dilute region of 500 2000 ppm, 2) the electrode potential of the metal substrate with respect to the equilibrium potential of the metal complex solution is slightly less noble, 3) the metal complex should be deposited by the electrode potential difference between the metal substrate and the metal complex. Further, in case of 1000 ppm of thiourea silver complex in aqueous solution, the same function can be observed.

(Discussion on the Meso-Crystal of Silver Oxide Compound: Part 1)

Figure 12A:
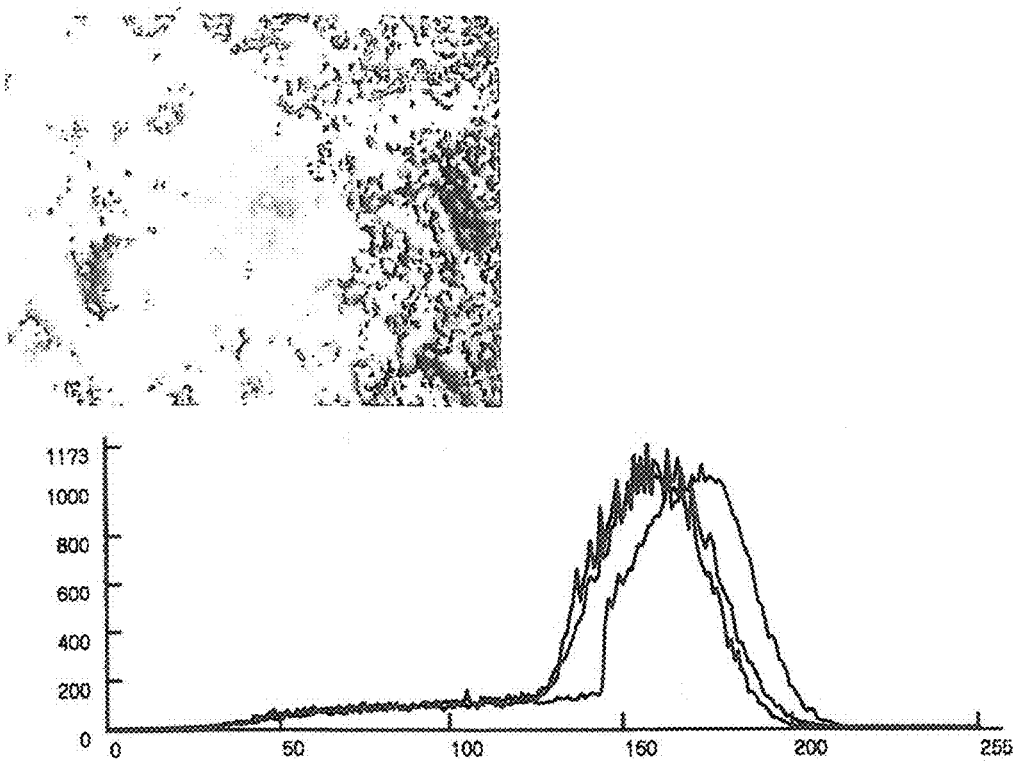
FIG. 12A shows a laser micrograph of a sample obtained by adjusting the serum obtained from benign disease patients and a histogram of the RGB.
Figure 12B:
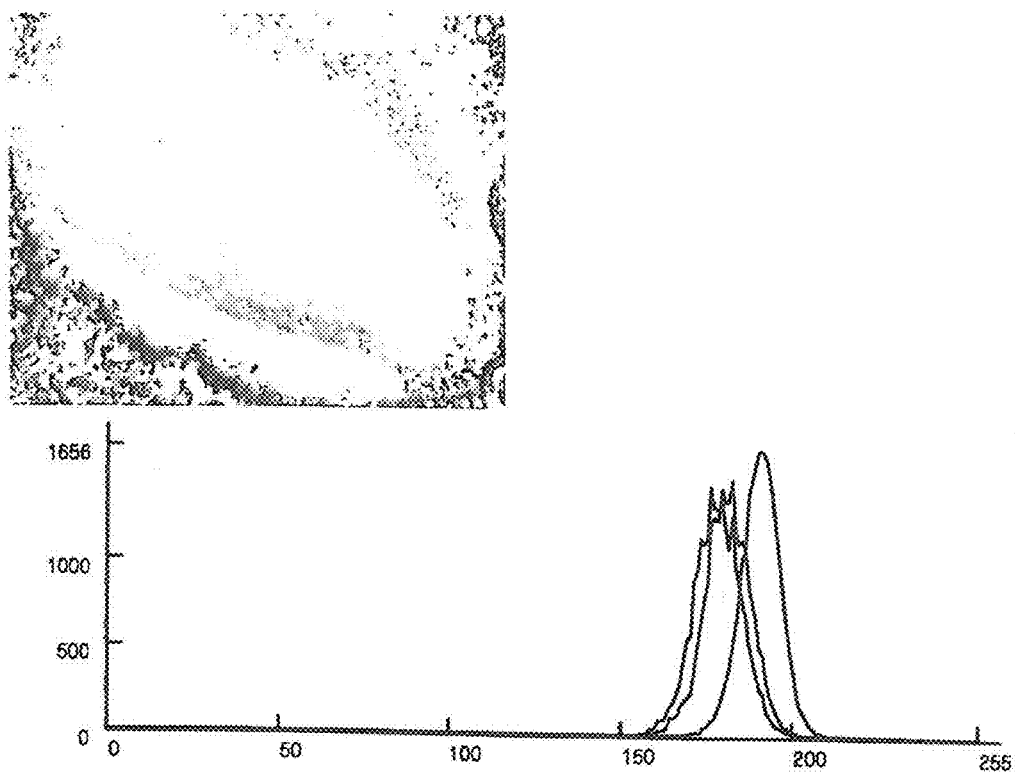
FIG. 12B shows a laser micrograph of a sample obtained by adjusting the sera obtained from gastric cancer patients and a histogram of the RGB.
Figure 12C:
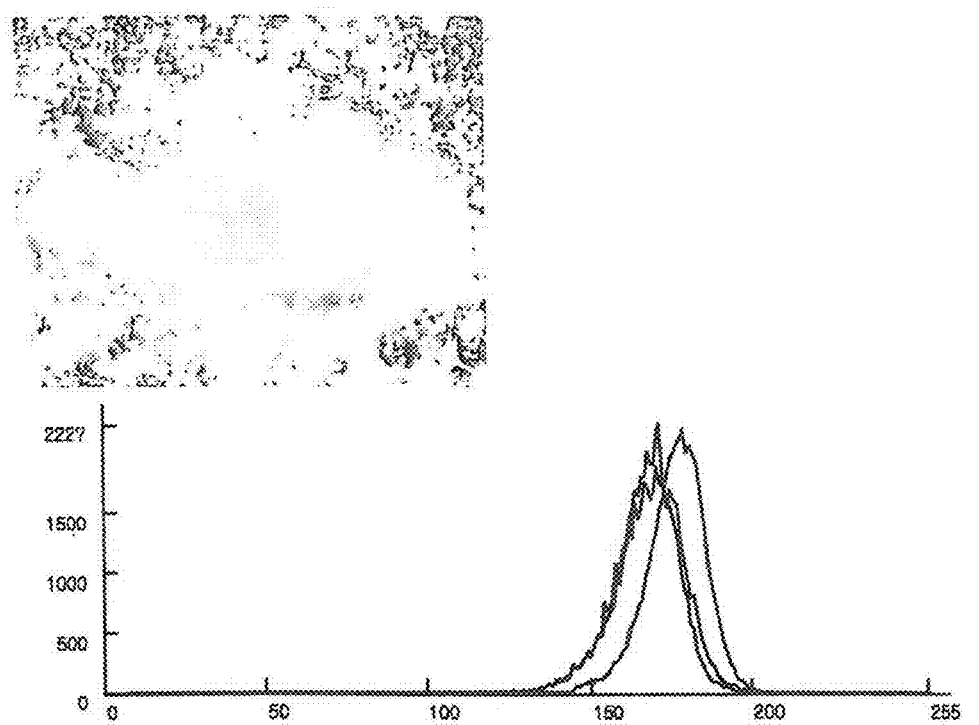
FIG. 12C shows a laser micrograph of a sample obtained by adjusting the serum obtained from colorectal cancer patients and histograms of RGB.

The quantum crystal substrate is subjected to a treatment of dropping 5% sodium hypochlorite solution thereon and the dropped solution is removed off 2 minutes later to obtain crystals having structures shown in FIG. 12, where needle-shaped crystals and large clumps such as rugby ball-like mass are observed and the respective compositions are subjected to analyzation at EDS spectra (elemental analysis). After a result of the analysis, the needle-like crystals are both considered to consist of a composite crystal of silver oxide and silver chloride, from the following reaction formulas and the result of FIG. 12 does not show any chlorine and shows that the silver and oxygen is dominant.

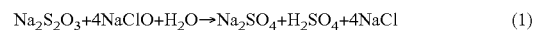

$$Na_2S_2O_3 + 4NaClO + H_2O \rightarrow Na_2SO_4 + H_2SO_4 + 4NaCl \quad (1)$$

$$Ag+ + NaCl \rightarrow AgCl + Na+ \quad (2)$$

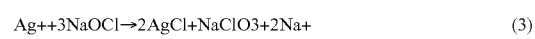

$$Ag+ + 3NaOCl \rightarrow 2AgCl + NaClO_3 + 2Na+ \quad (3)$$

$$Ag+ + OH- \rightarrow AgOH \quad (4)$$

$$2Ag^+ + 2OH- \rightarrow Ag_2O + H_2O \quad (5)$$

Thus, although it is considered that silver ions and thiosulfate ions are important in the formation of meso-crystal according to the present invention by alkaline oxidation reaction in the presence of chloride ions and, although the silver oxide is formed according to a conventional reaction, it is surprised that silver peroxide are predominantly formed from the following XPS measurement.

(Discussion of the Meso-Crystal of Silver Oxide Compound: Part 2)

Figure 13:
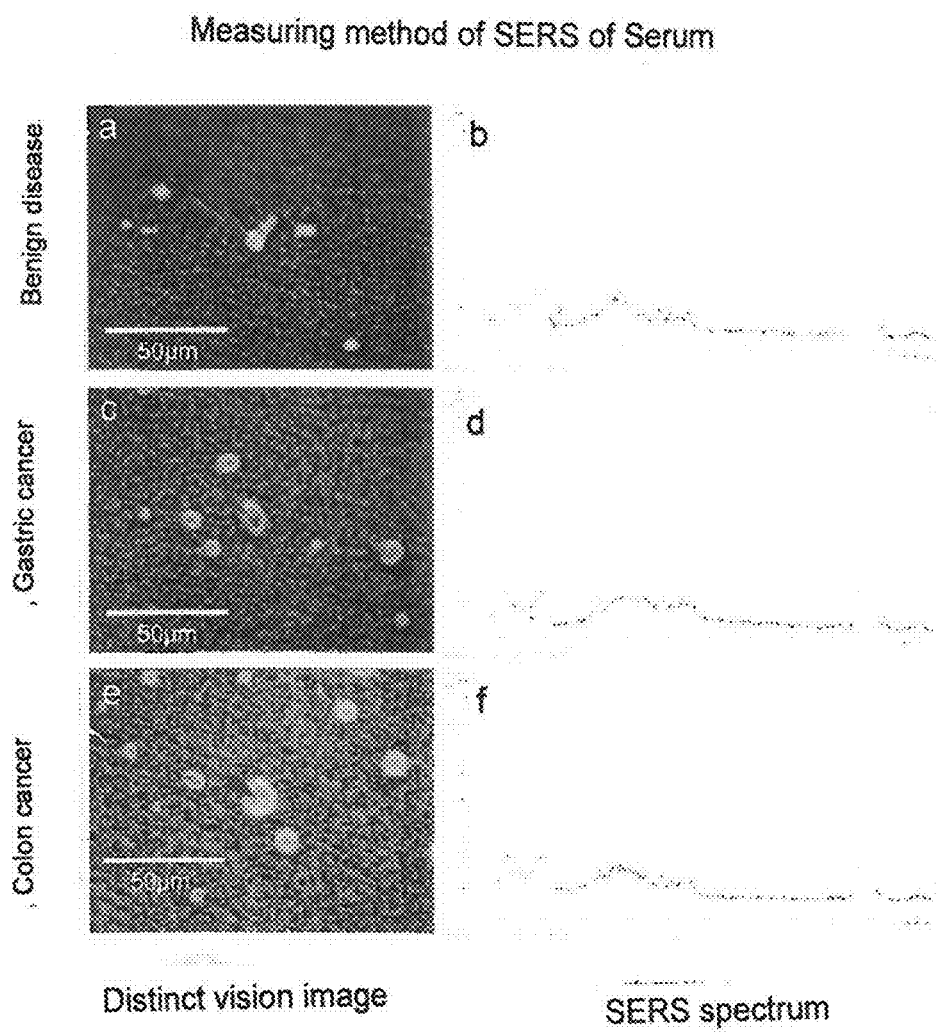
FIG. 13 shows plasmonic micrographs of distinct vision crystal display image and a method of measuring the Raman scattering spectra (unadjusted) of benign disease, gastric cancer, and colon cancer by aiming at the center of the crystals.
Figure 14:
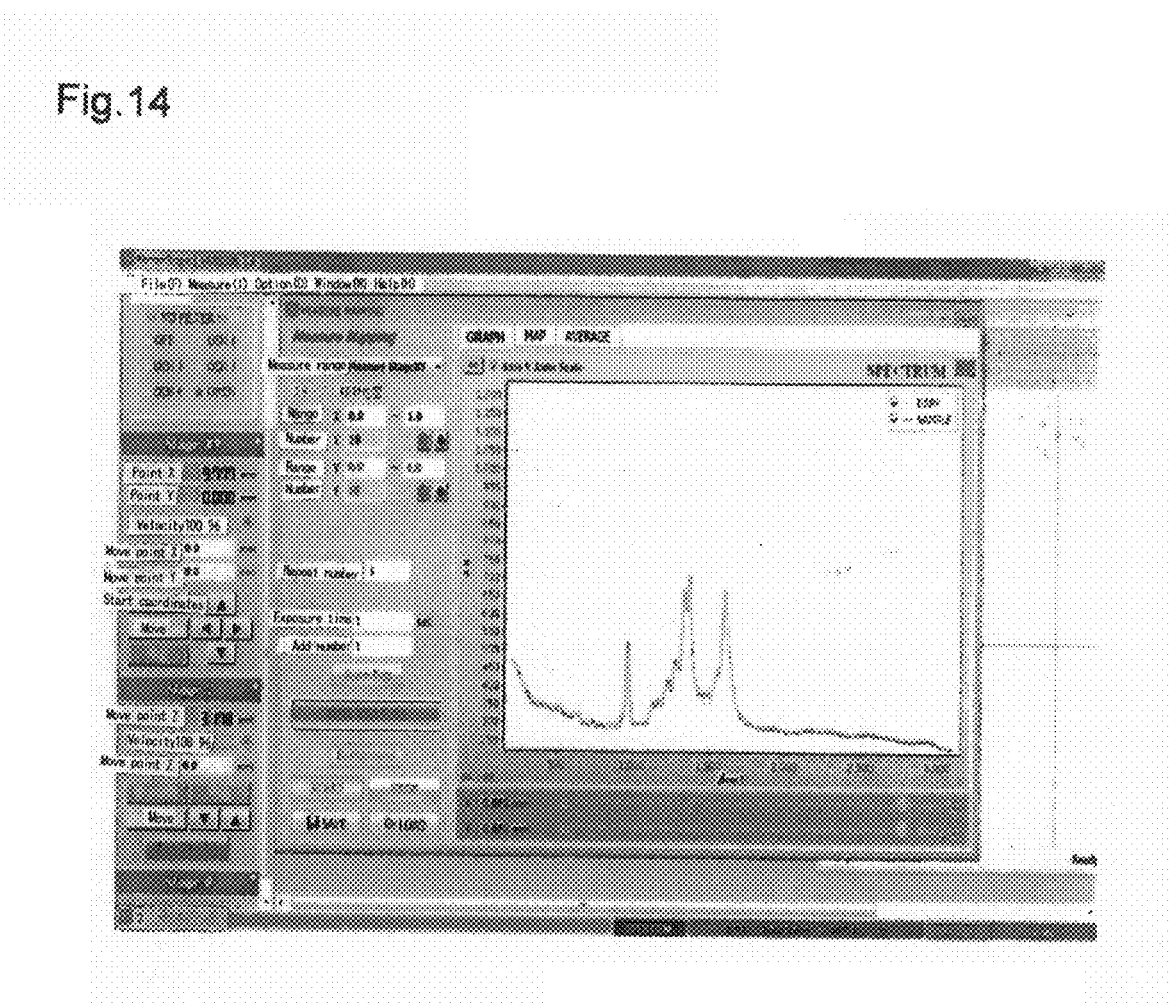
FIG. 14 shows Raman spectrum showing a state of chemical modification of histone tails of a gastric cancer-related substances.
Figure 15:
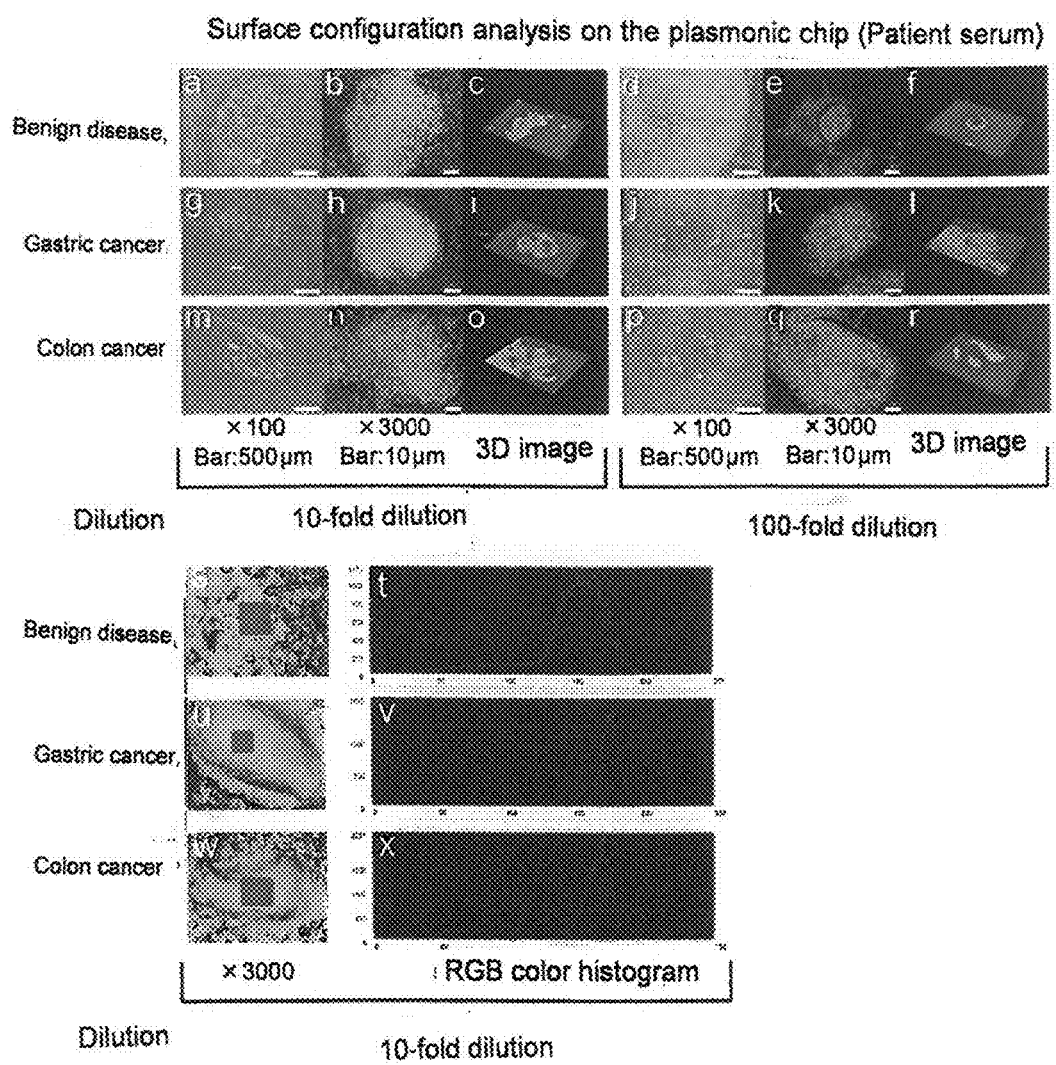
FIG. 15 shows 3D laser scanning micrographs (100-fold image, 3000-fold image and 3D image) of 10-fold dilution and 100-fold dilution samples of Benign disease (a, b, c; d, e, f), Gastric cancer (g, h, i; j, k, l), Colon cancer (m, n, o, p, q, r), 3000 times, it will show the 3D image. In addition.
Figure 16:
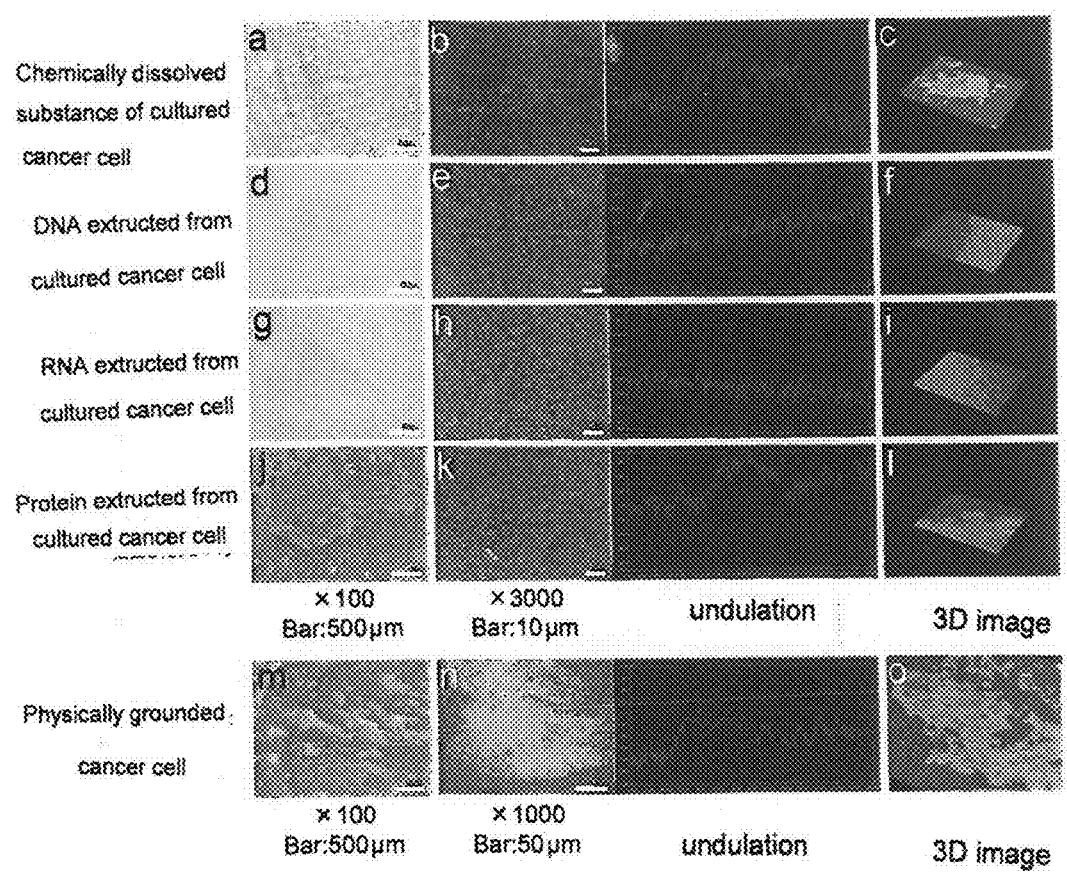
FIG. 16 shows photographs of 100-fold image, 3000-fold image with undulation, and 3D image in case of Kato-III (gastric signet ring cell carcinoma). Then, Kato-III was cultured and from the cancer cell double-stranded DNA, RNA and Protein were extracted, where the (a, b, c) are photographs of 100-fold surface image, 3000-fold surface image, and 3D surface image of the Kato-III (gastric signet ring cell carcinoma), while the (d, e, f) are photographs of 100-fold image, 3000-fold image, and 3D image of the DNA extracted therefrom. The (g, h, i) are also photographs of 100-fold image, 3000-fold image, and 3D image of the RNA. The (j, k, l) show photographs of 100-fold image, 3000-fold (images and undulations) and the 3D image of the Protein, while the (m, n, o) are photographs of 100-fold image, 3000-fold image, and 3D image showing a surface structure of physically grounded cancer cells.
Figure 17:
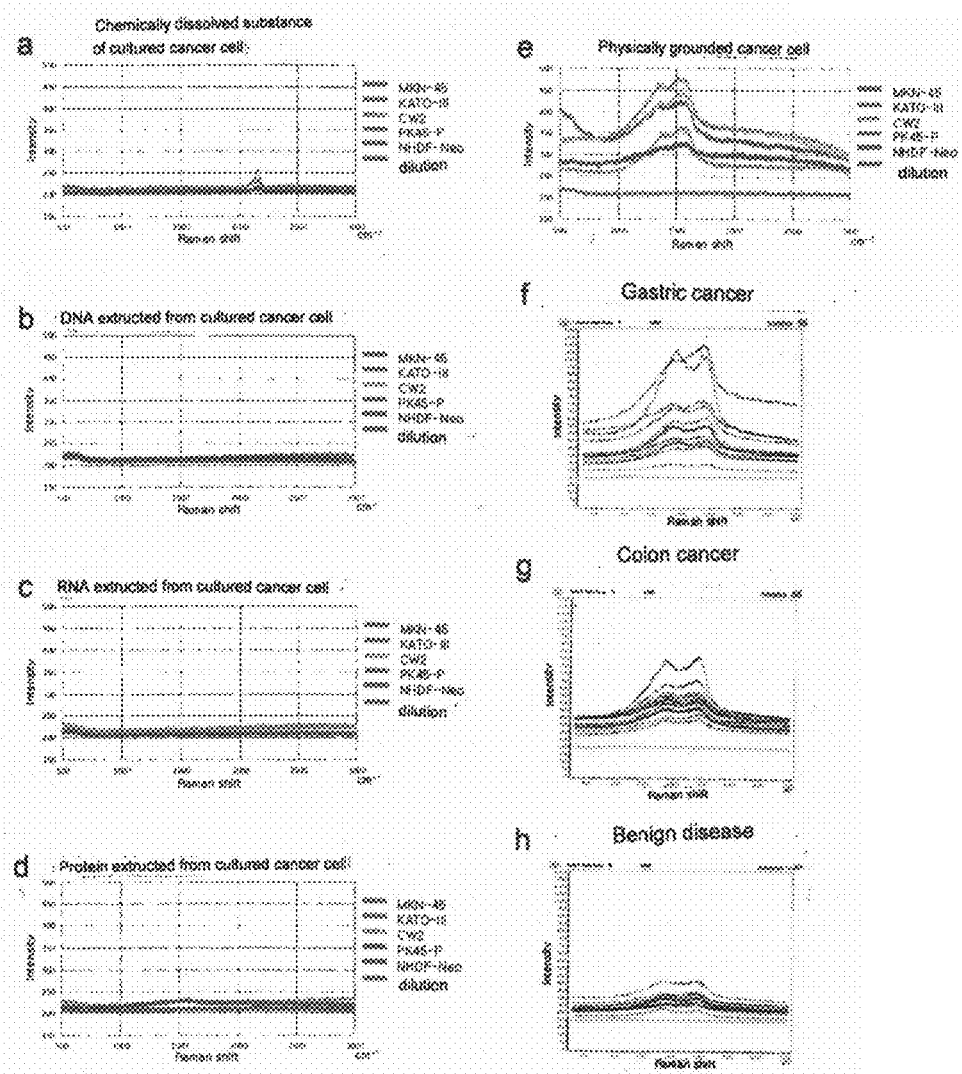
FIG. 17 shows Raman scattering spectra on the meso-crystal plasmonic chips where they are chemical cultured cancer cells (a), DNA extracted therefrom (b), RNA (c), Protein (d), physically crushed cancer cells (e), serum (f) from gastric cancer patients, serum (g) from colorectal cancer patients and serum (h) from benign disease patients, wherein Kato-III is gastric signet ring cell carcinoma, MKN-45 (poorly differentiated gastric cancer line), CW-2 (Japanese derived colon cancer cell line), PK45-P (human pancreatic cancer cell line), and NHDF-Neo (skin fibroblasts).

XPS Measurement:

The aqueous sodium hypochlorite was added dropwise for 2 minutes to the quantum crystal substrate prepared as the above, in order to make a re-crystal substrate, which is subjected to a XPS analysis (using models: ULVAC-PHI (Ltd.)/PHI5000 Versa Probe II (scanning X-ray photoelectron spectroscopy) without etching for Ag and O by XPS measurement. In addition, for comparison, Ag in the powder of silver chloride and the powder of silver oxide were measured. On the other hand, the recrystallized substrate was subjected to XPS measurement of Ag and O after etching for 5 minutes with an argon gas cluster ion gun. If the XPS measurement results of FIGS. 13 and 14 will be combined with the results of EDS according to FIG. 12, the peak in the vicinity of 529 eV is the peak derived from silver peroxide (AgO), while the peak in the vicinity of 530 eV is the peak derived from silver oxide (Ag2O). Further, if it is etched, the oxygen content decreases, while the O peak derived from the silver peroxide (AgO) in the vicinity of 529 eV is still greater than the peak derived from the silver oxide in the vicinity of 530 eV in case of etching, so that it is recognized that the silver peroxide was produced in the vicinity of the substrate. It is assumed that the electrode potential of the substrate and the catalytic action are affected to the meso-crystal formation.

The EDS measurement was carried out on the above-mentioned re-crystal substrate by using a JEOL Ltd./JSM-7001F (field emission scanning electron microscope analysis).

In addition, even if the aqueous solution selected from the group consisting of hypochlorous acid, 0.01 N sodium hydroxide, 0.01 N hydrochloric acid and 0.1 molar sodium carbonate would be used, any result similar to be treated with sodium hypochlorite was not obtained. Thus, it is believed that the formation of the needle-like crystals is caused by the above reaction in the presence of silver ions and thiosulfate ions. While the silver oxide is induced into negatively charged in an aqueous solution, it is reduced by the light to deposit metallic silver. Since silver peroxide shows more remarkable in the above tendency than silver oxide, it is possible to adsorb cancer related substances having a positive charge, resulting in occurrence of the surface plasmon enhancement effect between the trapped cancers related substance and the silver particles.

Figure 9:
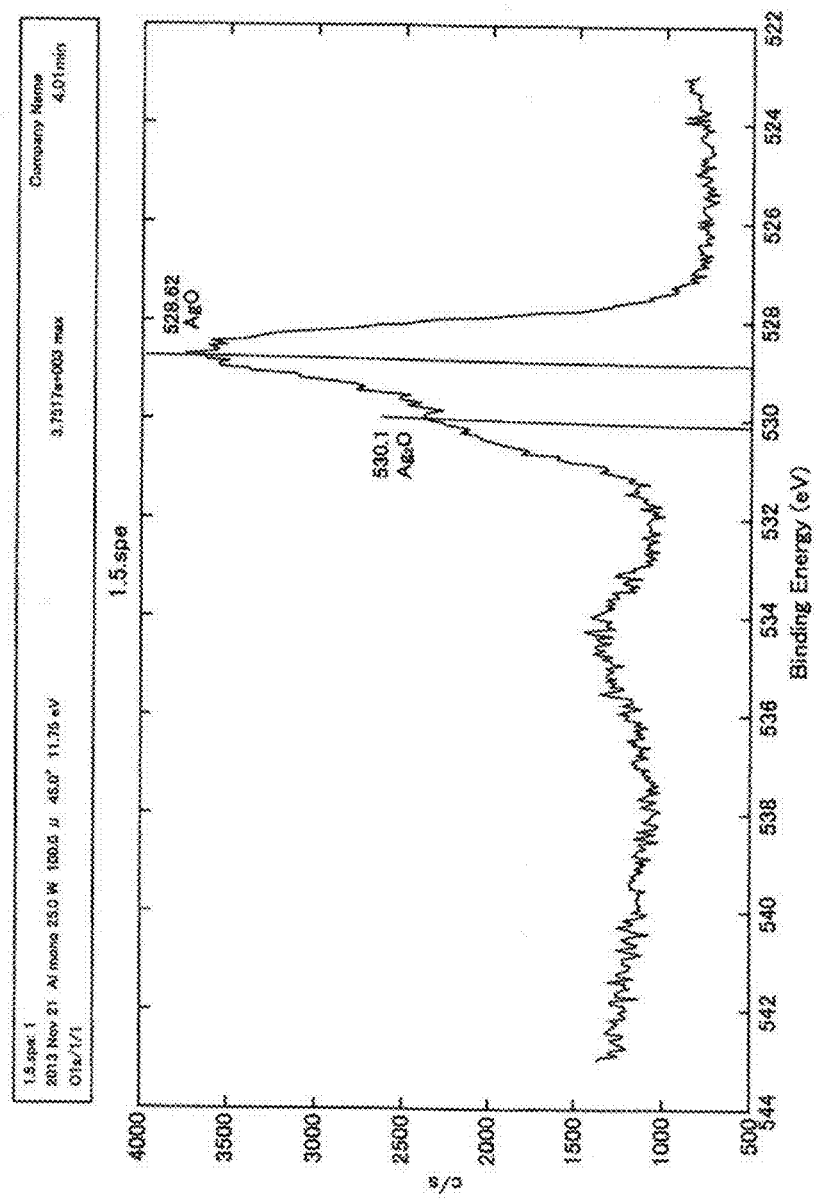
FIG. 9 is a graph showing a result of XPS measurement of the alkali-treated recrystallization substrate.
Figure 10:
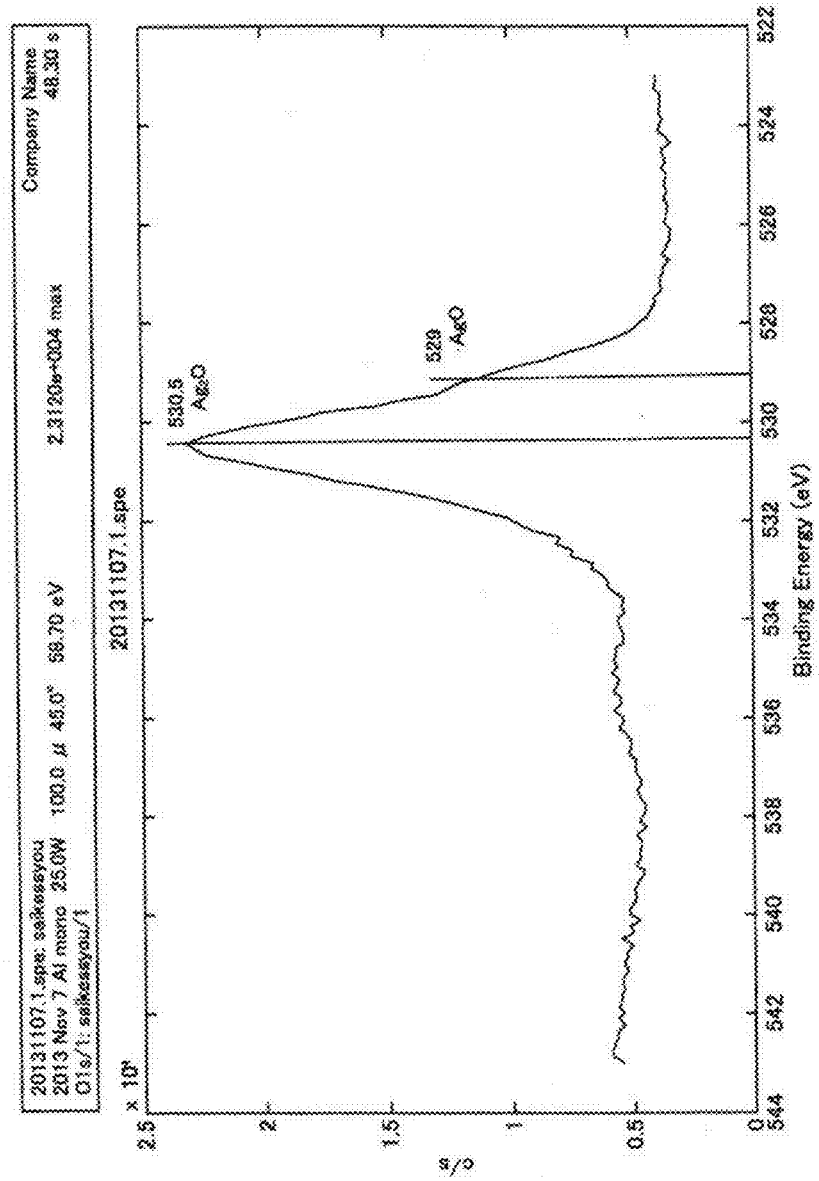
FIG. 10 is a graph showing a result of XPS measurements after etching the surface of the recrystallization substrate.
Figure 11:
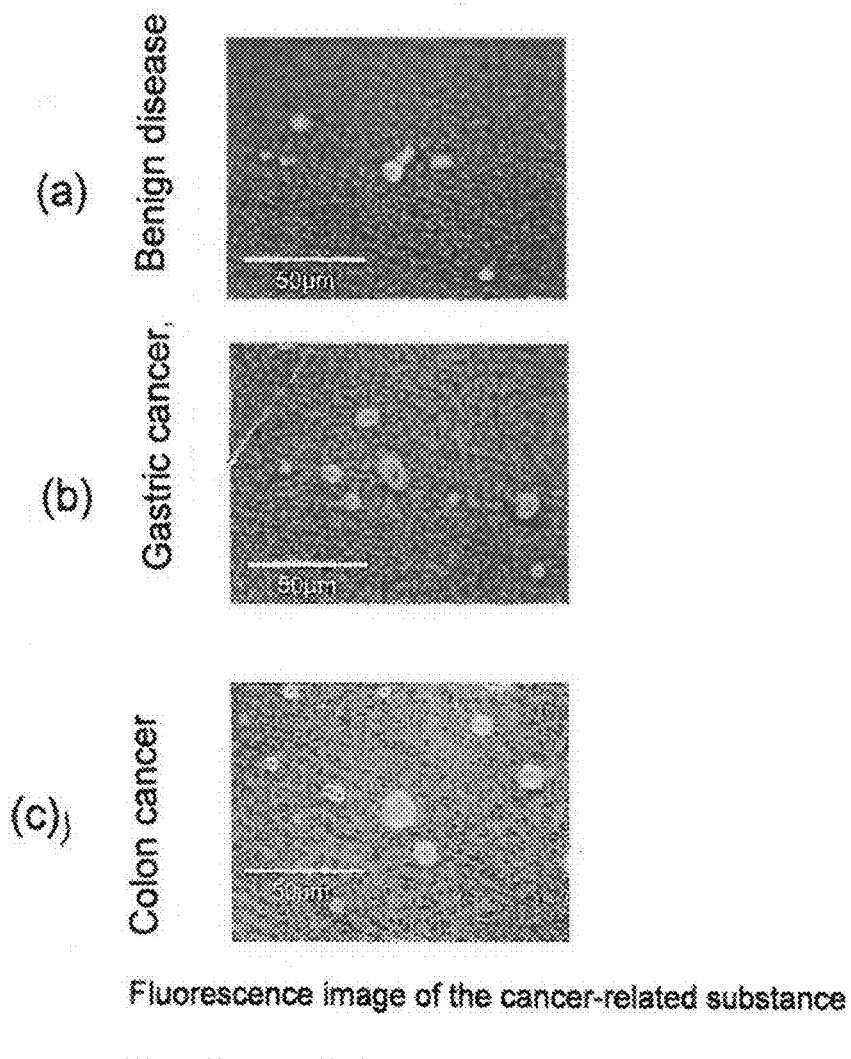
FIG. 11 shows fluorescence micrographs of the cancer-related substance adsorbed on the plasmonic chips in case of a benign disease, (b) a gastric cancer, (c) a colon cancer.

Moreover, according to the present invention, the plasmonic chip makes it possible to detect the presence and absence of cancer-related substances and analyze chemical modification factors that control chromatin remodeling by a diagnosis imaging and Raman analysis of biological samples including the blood. That is, these detection and analyzation can be carried out by the following steps which comprises a step of providing the plasmonic chip having a meso crystal region of the silver oxide containing silver peroxide (FIGS. 9 and 10) as the needle-like nanocrystal composites of the silver oxide containing silver halide or halogen, and a step of dropping the serum or biological sample solution onto the needle-like nano-crystal area of the plasmonic chip, whereby selectively adsorption of the cancer-related substances having a positive charge in the sample can be carried out.

(Diagnostic Imaging of Crystal on the Plasmonic Chip)

Figure 1A:
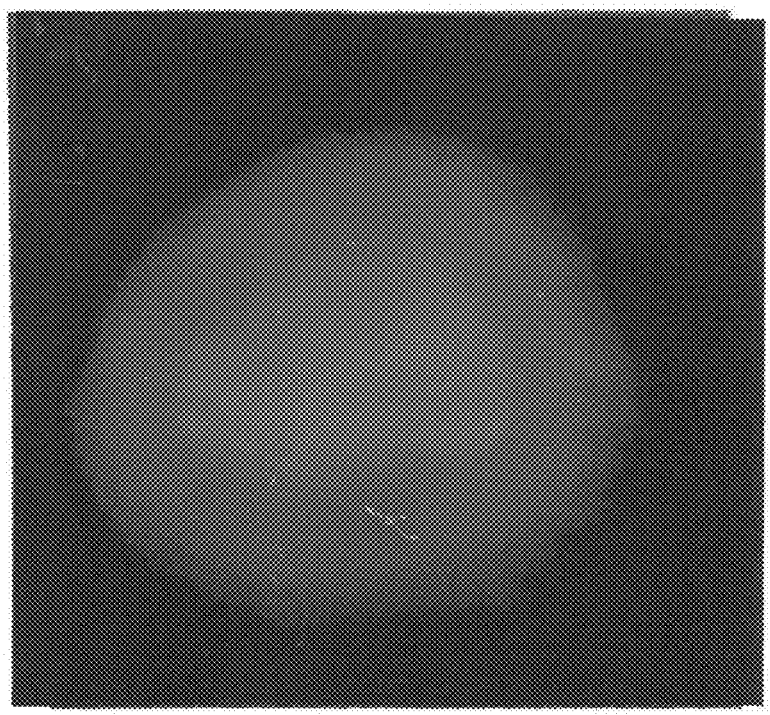
FIG. 1A shows fluorescence micrographs of the cancer-related substance of gastric cancer that adsorbed on plasmonic chip crystal by irradiation of UV (380 nm).
Figure 1B:
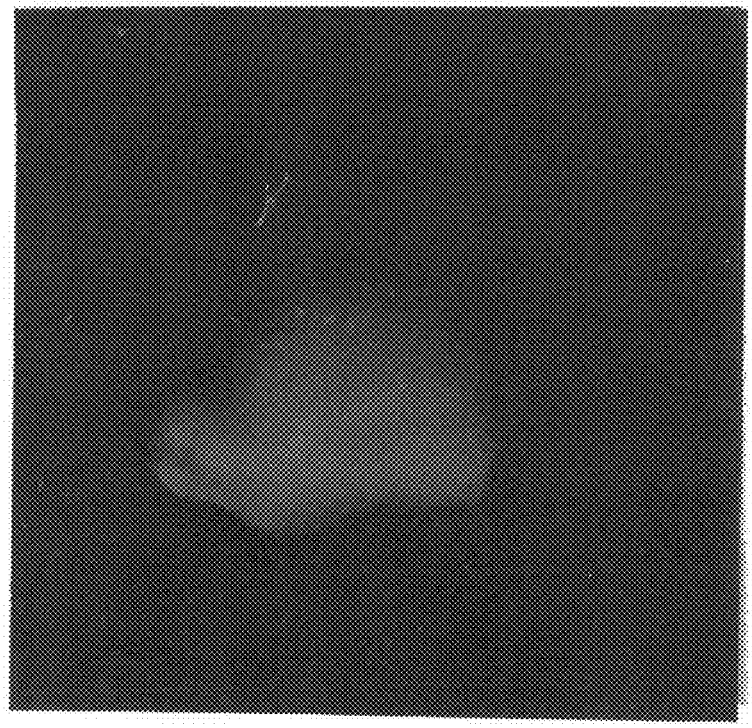
FIG. 1B shows fluorescence micrographs of the cancer-related substance of gastric cancer that adsorbed on plasmonic chips by irradiation of a red laser.
Figure 1C:
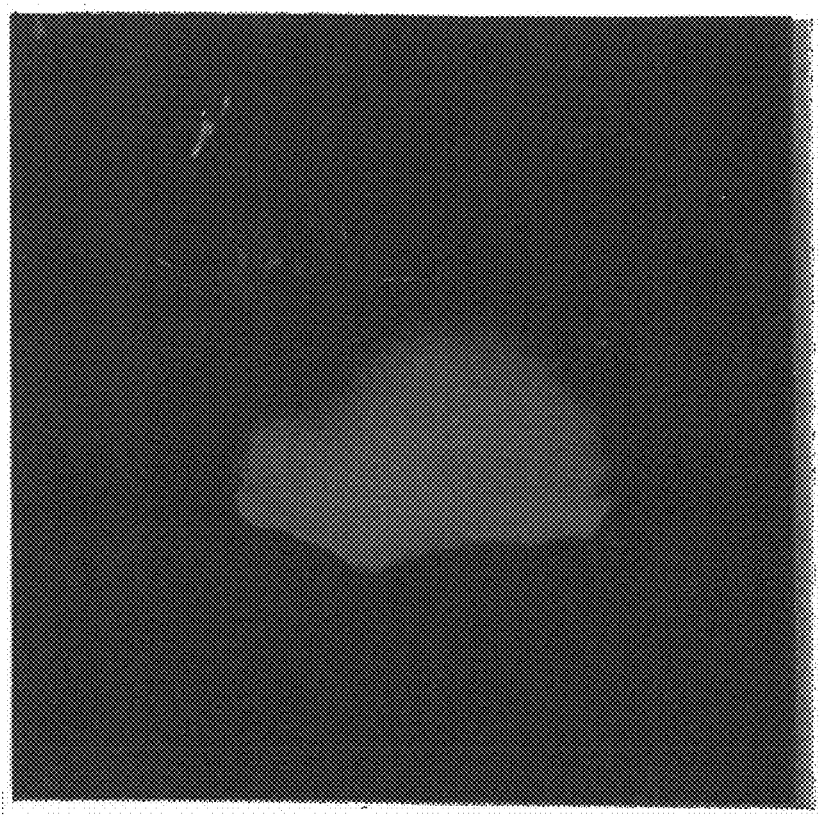
FIG. 1C shows the fluorescence micrographs of the cancer-related substance of gastric cancer that adsorbed on plasmonic chips by irradiation of a green laser.
Figure 2A:
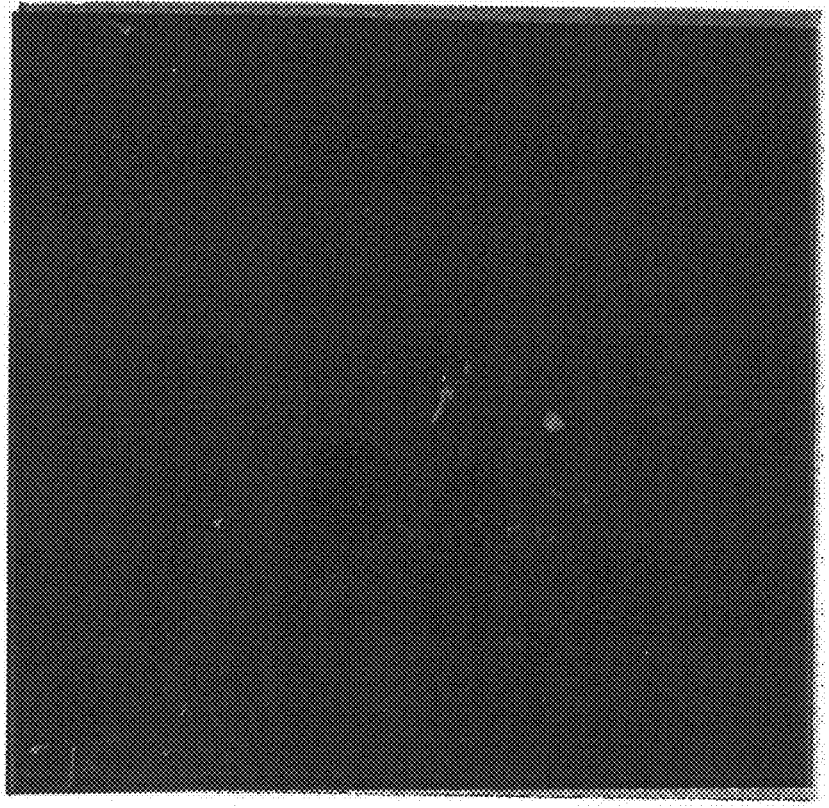
FIG. 2A shows the fluorescence micrographs of the cancer-related substance of colon cancer that adsorbed on plasmonic chips by irradiation of UV (380 nm).
Figure 2B:
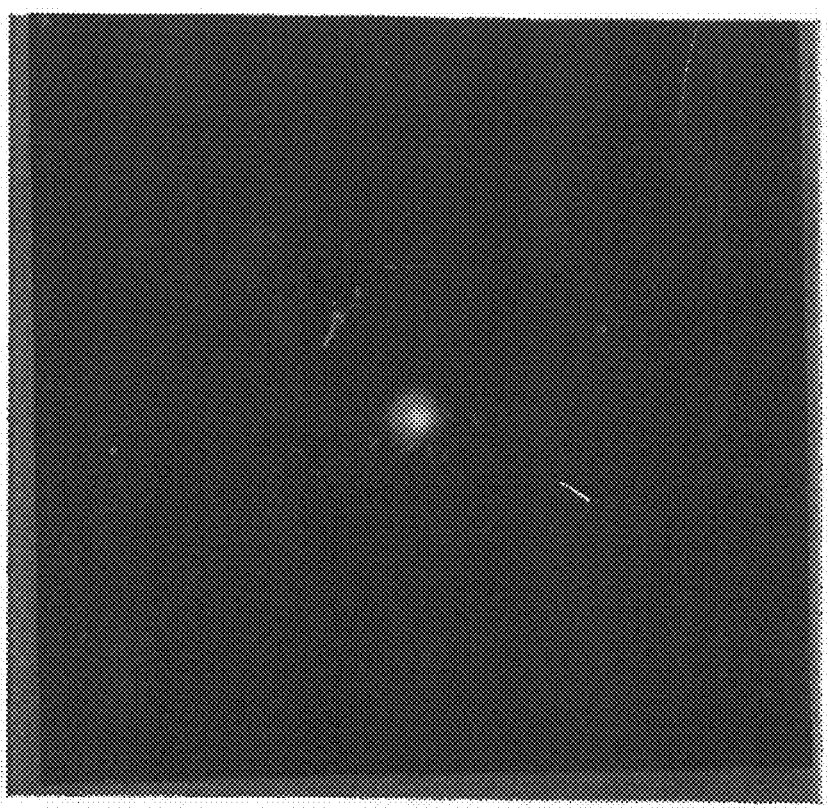
FIG. 2B shows the fluorescence micrographs of the cancer-related substance of colon cancer that adsorbed on plasmonic chips by irradiation of a red laser.
Figure 2C:
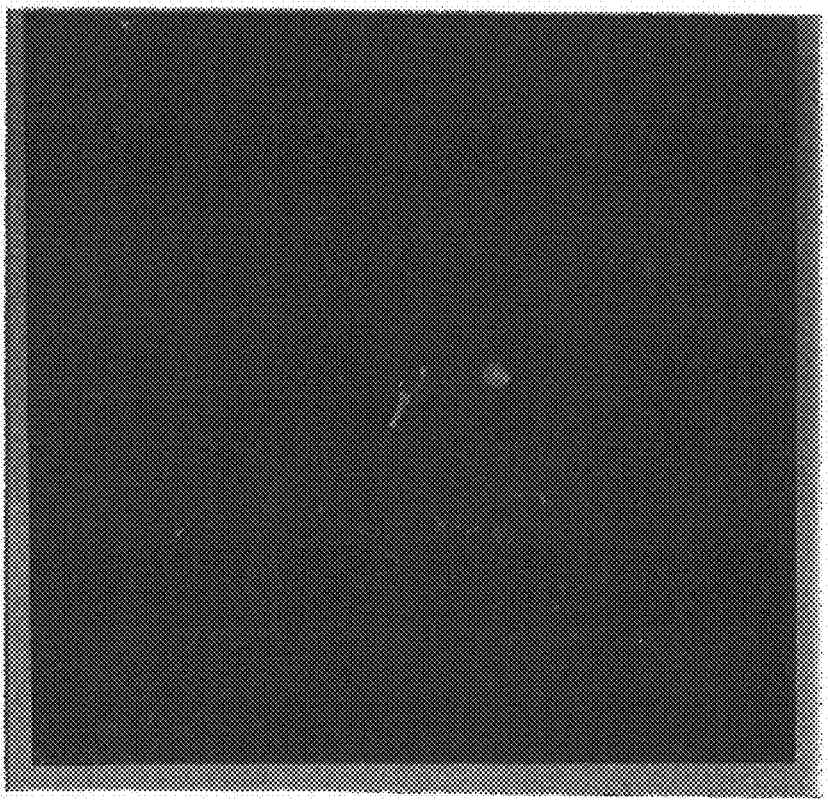
FIG. 2C shows the fluorescence micrographs of the cancer-related substance of colon cancer that adsorbed on plasmonic chips by irradiation of a green laser.

The adsorbed cancer-related substances were observed by a reflection microscope (magnification 500-fold). The crystal images of the cancer-related substances in case of a benign disease, a gastric cancer, and a colon cancer are shown (FIGS. 1 (a), (b) and (c)). The image information such as the area of the crystal of the image, the volume, the length, the width and so on can be digitized and these numbers are used for the histogram. Observation of images with 15,000 fold by a laser microscope (VK-X250 shape analysis Laser microscope manufactured by Keyence Corporation) are shown in FIGS. 2A, 2B, and 2C, where there can be observed differences between the benign disease and the stomach cancer or the colorectal cancer. Graphing of R, G, and B in the histogram, as shown in FIGS. 2A, 2B and 2C, makes the peak deference clear relating to the position and the shape between the benign disease, the stomach cancer, and the colon cancer. Therefore, it is understood that use of the plasmonic chips provided with meso crystals containing silver peroxide makes it possible to identify the presence of cancer by selectively capturing the cancer-related substances in blood. Further, use of a confocal laser microscope is preferable, since the slice image and then the internal information are obtained.

(Auto-Fluorescence Imaging Diagnosis of Crystal on the Plasmonic Chip)

In addition, sera obtained from benign disease patients (esophageal achalasia, gastric mesenchymal tumor, duodenum benign tumor) and sera obtained from cancer patients (stomach cancer, colon cancer, pancreatic cancer) were subjected to auto-fluorescence imaging diagnosis on the plasmonic chips with a fluorescence microscope. It is understood that clear identification can be made between the benign disease patients and the cancer patients, depending on whether auto fluorescence can be observed or not as shown in FIG. 20.

(Raman Analysis of Crystal on the Plasmonic Chip)

Figure 3:
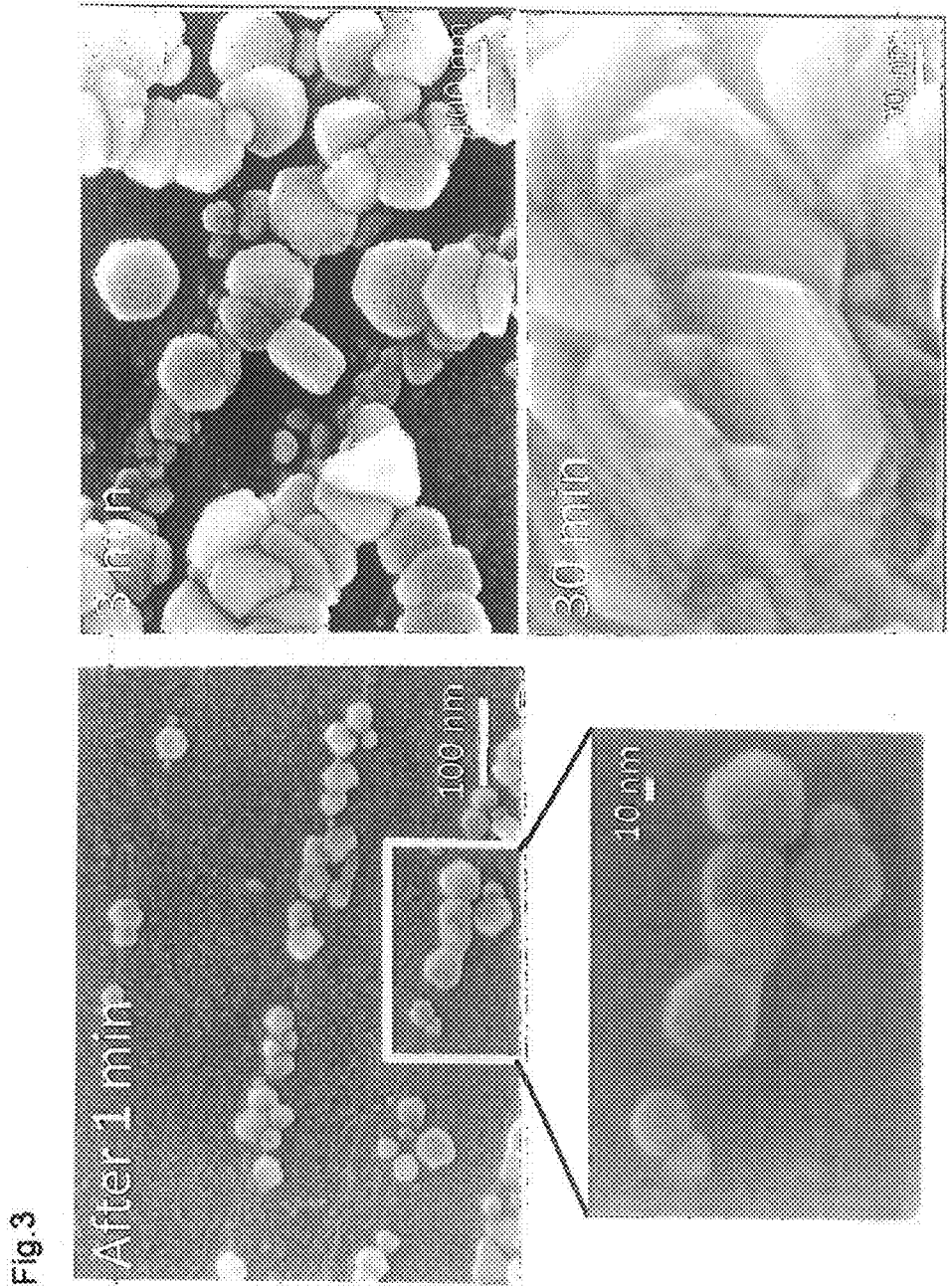
FIG. 3 is a photograph showing the relationship between quantum crystal shapes and standing times after dropping on the phosphor bronze substrate.
Figure 18:
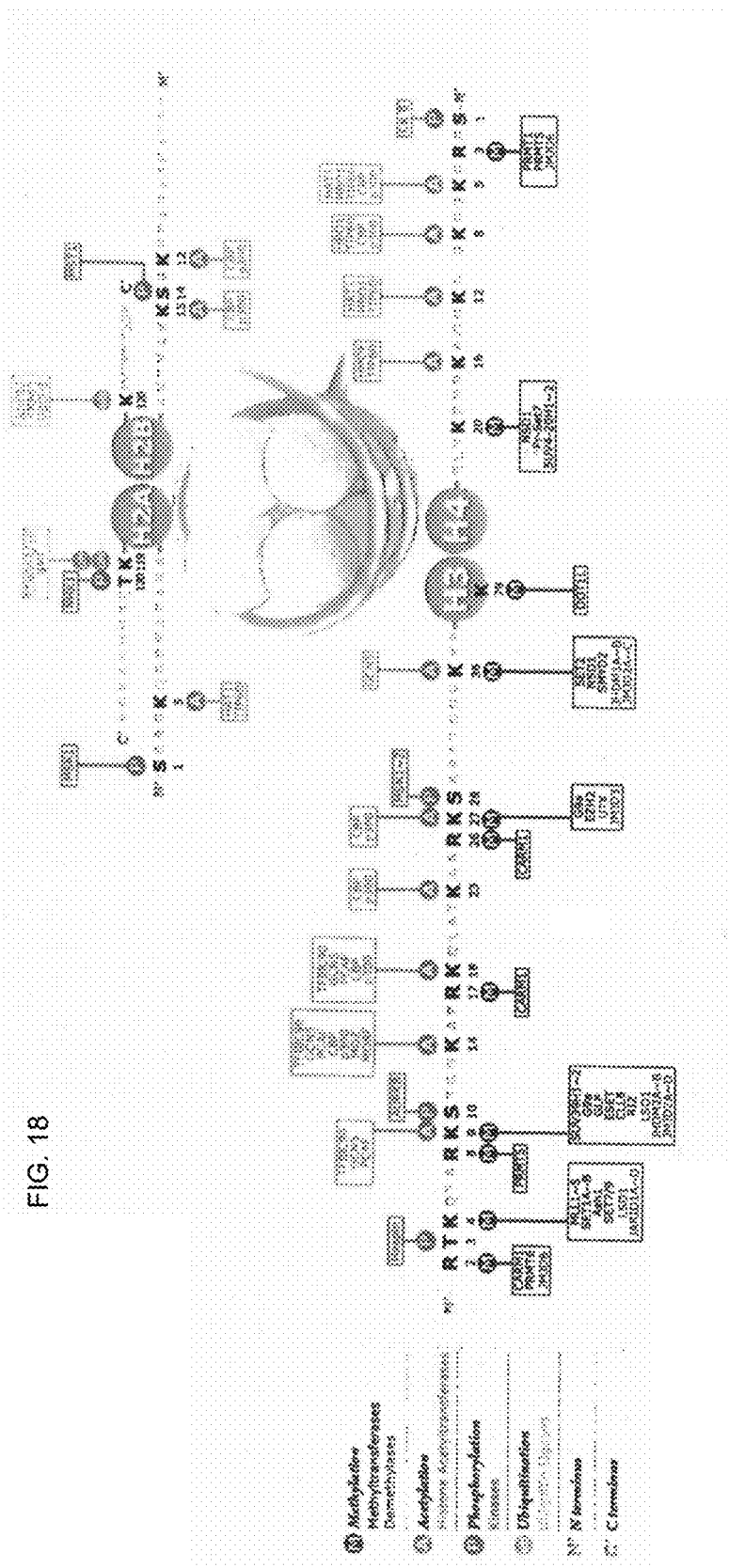
FIG. 18 shows histone-associated antibodies diagram for identifying a chemical modification of histone tails (referring to www.genetex.com).
Figure 19:
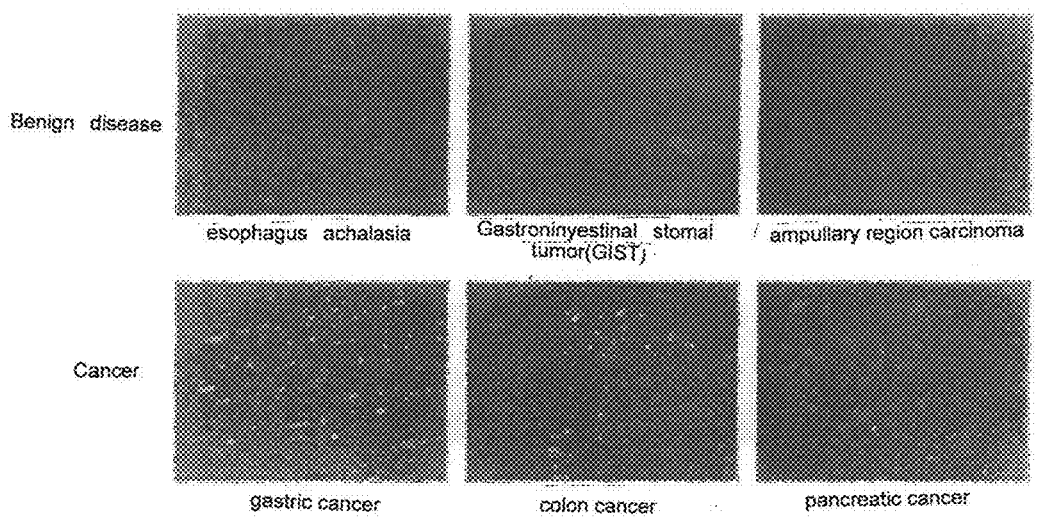
FIG. 19 shows a fluorescence image showing the auto fluorescence state of benign disease and cancer, which is observed on plasmonic chip of the present invention.

Crystals of adsorbed cancer-related substances on the plasmonic chips cannot be observed with naked eyes. Under a microscope (500-fold), crystalline mass are observed like distributed points (FIG. 18). Laser Irradiation to one of the crystalline mass (wavelength 532 nm) makes Raman spectra from there, where it is possible to determine the cancer disease with the intensity of surface-enhanced Raman scattering (SERS). FIGS. 3 (a), (b), and (c) show the Raman spectrum obtained therefrom by irradiating laser (wavelength 532 nm) to in case of benign disease, gastric cancer, and colon cancer. In particular, FIG. 4 is an enlarged view of the Raman spectrum in the case of gastric cancer, where the chemical modification of the histone tail can appear as peaks and can be determined in so called fingerprint region from 1300 $cm^{-1}$ less than 625 $cm^{-1}$.

The cancer-related substances in the serum, may include a DNA that wraps around the histone derived from cancer cells, a histone wounded around with DNA (so called nucleosomes) and also a chromatin (fiber) where histones gather and form a string-like structure. It is indicated that the substances to be detected in the present invention are deemed to be the cancer-related substances in the light of their increasing volumes because although globulin is positively charged, the globlin increases up to 2 times at most, while the cancer-related substance increases up to 100 times in association with progression of the cancer. Moreover, DNA left from the normal cells, DNA dissociated from histones by acetylation and albumin account for approximately 60% of serum, but owing to their negative charge, they will not be absorbed or captured in the present invention. Therefore, it is advantageous for fluorescence imaging of cancer-related substances and it is convenient to analyze the chemical modification of histone tails by Raman spectroscopy.

Moreover, needle-like nanocrystals of the present invention (meso crystals of the silver oxide containing silver peroxide) is easily negatively charged in aqueous solution and it is believed to form a charge transfer complex in contact with the sample (target molecules). Furthermore, the silver oxide is reduced by receiving a light energy to be changed to metallic silver, and will make a localized surface plasmon resonance enhancement effect with the metal nanoparticles arranged regularly. Therefore, needle-like nanocrystals of the present invention (meso crystal), although it is a non-metal, are provided with the metal property as well as the ionization property, which is suitable for a plasmonic chip used for measurement of surface-enhanced Raman scattering (SERS), as a cancer diagnostic chip.

On the other hand, quantum crystals formed on a metal substrate or metal particles are believed to likely have a positive polarity in an aqueous solution as a metal complex crystals, so that in order to adsorb proteins in a biological sample, an alkali treatment in the presence of halide ions is preferable to adjust the polarity by dropping sodium hypochlorite solution having pH11 or more. Quantum crystals can be recrystallized not only to have a negative polarity in an aqueous solution, but also to make a needle-like composite of nanocrystal silver oxide including silver peroxide, so that immobilization of histones having a positive charge can be promoted as cancer-related substance.

(Image Diagnosis of Histone Tail)

Nucleosomes is a basic building block of chromatin, where DNA is wound to histone octamer consisting of four histone (H2A, H2B, H3, H4) to have a role of packaging the DNA and also a role of regulating the accessibility of the DNA to play an important role in gene regulation. The histone post-translational modifications, controls interactions with DNA and other nuclear proteins to affect the reversible gene expression. As types of histone modification, there are mainly known methylation, acetylation, phosphorylation, ubiquitination, SUMO reduction, citrullination, and ADP-riposylation. In the sequence of histone, depending on which part is subjected to these modifications, the periphery of the gene expression is activated or inhibited. The relation between combination of post-translational modification sites of histones and gene expression can be tested and verified with histone code associated antibodies (Genetex Inc. anti-histone antibody), and by Raman spectroscopy as well as observation in the fluorescence images modified state of histone code that is captured by the plasmonic chip of the present invention and then verification of the histone code hypothesis can be carried out. The histone code hypothesis is now described as follows.

(Histone Code Hypothesis)

Histone code hypothesis has been proposed in relation to the chromatin remodeling by Dr. Alice group of Rockefeller University. That is, the chromatin remodeling is defined as the following phenomenon, where associated with molecular mechanism through changes in chromatin structure which modulates the expression levels of genes, and with the induction, 1) change in the histone modification, 2) change in the methylation status of genomic DNA, then associated therewith 3) phenomenon in which changes in the high sensitivity region occur against DNase. The present inventors have, based on the histone code hypothesis, in order to elucidate the mechanisms of cancer development, an intensive research has been carried out, where as cancer-related substances, the nucleosomes and chromatin relating to histones firstly is selectively captured and then tried to verify this. Most of genomic DNA are wound in core histone, and is stored as chromatin. Therefore, nuclear phenomena which directly encourage to genomic DNA such as transcription, replication, repair and so on, is accompanied by chromatin structural changes in some way. This chromatin remodeling in a broad sense is to control the nuclear phenomenon in reverse. For example, transcriptional activity varies within a scope up to about 2500-fold, depending on the chromatin structure. Since the range of the activation of the transcription factor in the naked DNA is a 10-fold, most of the transcriptional control is done in chromatin remodeling. Among the factors involved in the chromatin remodeling, histone modification factor such as acetylation, phosphorylation, methylation, ubiquitination and their removal performance, make histone H3, H4 amino terminal side to form a chemical modified pattern. This chemical modified pattern acts as a recognition code and then the factors that further involved in remodeling is recruited. This is proposed as "histone code hypothesis".

The structural biology is said to have played a large role for the verification of the "histone code hypothesis" where a histone tail received this chemical modification serves as a recognition code such as remodeling factors. For example, most of HAT, ATP-dependent remodeling factors, coactivators, TFD subunit TAF, are provided with a low-bromo-domain homology consisting of about 110 amino acids. The bromo domain structure of the coactivator P/CAF is determined by NMR, so distinctive hydrophobic pockets have been found. Results of the binding experiments with NMR, showed that the pockets were bound to peptides of histone H3 tail acetylated. Also, the crystal structure provided with two-bromo-domains arranged in tandem of TAF 250, is the largest subunit of the general transcription factor TFD. This structure has an activity of binding to the tail of histone H4, which is modified with acetylation. Also, chromo domains of heterochromatin protein 1 has been shown to bind to histone H3 tails methylated. NMR structure of the chromo domain of mouse chromatin modifier protein 1 has been reported. This chromatin remodeling factors may be accessed directly to specific nucleosomes sites by recognizing codes of histone tail with bromo domain. This chromatin remodeling factors are often indirectly recruited by a DNA binding transcription factor. The transcriptional repressor Mad having bHLH (basic helix-loop helix)-Zip as the DNA-binding domain, recruits Sin3 complex containing histone deacetylase as a sub-unit into the chromatin. Complex of PAH2 domain and transcriptional repressor domain of the Mad the Sin3 is analyzed by NMR and the recruitment mechanism for the chromatin region of deacetylation complex has been discussed.

It has been believed that DNA methylation is involved deeply in this chromatin structure control. In the genomic DNA sites that DNA methylation is seen at a high density, generally the chromatin structure becomes strong, reduction of transcriptional repression and DNA mutation rate is observed. Also, it has been reported that methylation patterns and genomic imprinting of genomic DNA, the X chromosome inactivation and cell cancellation have a clear correlation each other (referring to non-patent document 1). Therefore, it can be said that structural analysis of histones and chromatin holds the key to explain the context of cancer, so that analyzation of the chemical modification factors of histone tails has a great significance. Since histones and chromatin can selectively absorbed or captured according to the present invention, not only a means of fluorescently labeled chemical modification status of histone code but also a means of Surface enhanced Raman spectrometry (SERS) can be provided.

(Chromatin Remodeling)

Meanwhile, the genomic DNA is a body of genetic material is a 2 m long thing in humans, which is housed in the small space of 100 femto-liters of a so called cell nucleus. Storage of such genomic DNA can be accomplished by molecular complex called "chromatin". The foundation structure of chromatin is a "nucleosomes" where histone protein is wound around with DNA and those nucleosomes are beaded, and further folded highly bound to proteins and RNA to form a "higher-order chromatin". However, Unravelling of the DNA from chromatin, requires a large energy, so chromatin is inhibitory to the functional expression of the DNA, such as replication, transcription, and recombination. But organisms, through the dynamic variation of chromatin, very easily makes replication, transcription, and recombination. It is said that this "dynamic chromatin structure" is being produced by a variety of the nucleosome structure by histone variants and modifications, the diversity of its arrangement, and the interaction of the complex between protein and RNA molecular, while it has been controlled by the interaction of cell nuclear structure, nuclear membrane, and nuclear pore complex. To explain the phenomenon, DNA of eukaryotic organisms, was tightly bound to the histone protein synthesized in the body to form a nucleosome and the helix of nucleosomes form a strong chromatin structure. In case of the histone and DNA tightly combined, it is difficult to RNA polymerase to bind to DNA. On the other hand, when the transfer is thriving, the chromatin structure becomes loose and histone from nucleosomes is released out to let DNA naked. When the transfer is suppressed, on the contrary, the nucleosome structure is solid while the chromatin is gathered. Restructuring or reconfiguration of the chromatin structure means such a chromatin remodeling described above but the promoter and enhancer promote transcription and enhance gene expression. One of these roles is to loosen the binding of histone and DNA, sometimes to destroy the nucleosome structure, which promote the RNA synthesis by RNA polymerase. In detail, on the histone tails at the end of the translated histone protein, a lot of basic amino acids (positive charge) is present. The basic amino acids are electrostatic binding to the DNA of a phosphate group (negative charge). To loosen the binding of histones and DNA may lower basicity of histones into weak. Transcriptional regulation by chromatin remodeling is actually made by a complex reaction in which many kinds of enzymes and proteins involved in transcription factors bind to promoters and enhancers, bond to histone acetylation enzyme (HAT: histone acetyltransferase) which enzyme makes acetylation of the amino group of histone. The acetylated amino group lowers the basic which causes weak binding to the DNA. After this, a dissociation of histones with DNA further progresses and further the acetylation of histones progresses, resulting in reveal of the promoter which makes it easy to combine with RNA polymerase. Therefore, it is important how to trap the cancer-related substances in the body fluid and how to analyze it in order to elucidate the mechanism of chromatin remodeling based on histone code hypothesis.

According to the plasmonic chip of the present invention, trapping of the histones and chromatin as a cancer-related substance, the presence or absence of cancer symptoms can be judged by the fluorescence imaging depending on volumes of the crystal. Then, the cancer symptoms come from any organ, and how the cancer progresses can be determined by analyzing the remodeling factors and chemical modifications of histone tails. And, all the information relating to how the cancer occurs and how the cancer progresses through this chromatin remodeling events, make it possible for doctor to predict accurately specific chemotherapeutic agents, and also to rationally design chemotherapy based on knowledge of tumor chemo sensitivity.

Here, a protein of cancer-related substances of interest to be detected is a histone wrapped around with DNA. The unit structure is called a nucleosome, and the string form structure made of nucleosome gathered is called a chromatin (fibers). And, in time of repeat of dividing cancerous cells, methylation modification makes DNA to wrap around histone not to come out from bad genes (tumor suppressor gene). Usually histones show (+) charged, while DNA show (−) charged, so that histone and DNA stick each other as a magnet and methylation improves untied, where DNAs winding around the histones are charged (+) (see FIG. 8 (a)). On the other hand, acetylation makes it (−) charged, so that histone acetylation makes DNA of (−) and histone (−) repelled each other. Then, the 'thread' of DNA has a mechanism for expression of the gene unwound from the histones (see FIG. 8 (b)). Therefore, in order to selectively adsorb the cancer-related substances derived from cancer cells, the substrate to be adsorb is preferable to be (−) charged since the histones wound around with DNA is (+) charged.

INDUSTRIAL AVAILABILITY OF THE INVENTION

Thus, according to the present invention, the cancer-related substances in blood and biological samples can be selectively detected through auto fluorescence by localized plasmon enhancement effect. Further, it is also possible to determine the existence of cancer simply through fluorescence microscopy because the cancer-related substance with a variety of fluorescent labels can be selectively captured. Furthermore, since chemical modification status of histone tails can be detected from the Raman spectrum of the crystals with or without labels, it is also possible to carry out early detection of cancer, and determination as to progression of the cancer. Therefore, summarization of the usage way according to the present invention is as follows.

What is claimed is:

1. A plasmonic chip, comprising:
a region of meso-crystal including nanocrystals of silver oxides containing silver peroxides, wherein
the meso-crystal is able to have a function to generate a negative polarity when the meso-crystal is in contact to sera or biological samples, to selectively capture or absorb a cancer-related substance having a positive polarity, and to show an effect of localized surface plasmon resonance when the meso-crystal is irradiated with light.

2. The plasmonic chip, according to claim 1, which is used for observing a cancer-related substance, wherein the meso-crystal including nanocrystals of silver oxides containing silver peroxides is a needle-like crystal made from silver complex quantum crystal by alkali treatment.

3. A method of observing a cancer-related substance, comprising:
providing the plasmonic chip which comprises a region of meso-crystal including nanocrystals of silver oxides containing silver peroxides;
dropping a serum or biological sample by itself or dilution sample on the crystal region of the plasmonic chips, to generate a negative polarity in contact to the serum or biological sample so as to selectively capture or adsorb cancer-related substances in the serum or sample; and
observing, in image, the cancer-related substance enhanced by localized surface plasmon resonance.

4. The method of observing a cancer-related substance according to claim 3, wherein the cancer-related substance is a nucleosome or chromatin including the histone wrapped around with DNA.

5. The method of observing a cancer-related substance according to claim 4, which further comprises a step of irradiating a laser light on a nucleosome or chromatin including the histone wrapped around with DNA.

* * * * *